US012799462B2

(12) United States Patent
Shim et al.

(10) Patent No.: US 12,799,462 B2
(45) Date of Patent: Nov. 17, 2026

(54) MXENE OR DERIVATIVE THEREOF IMMOBILIZED WITH NITROUS OXIDE REDUCTASE AND USE THEREOF

(71) Applicants: Samsung Electronics Co., Ltd., Suwon-si (KR); Konkuk University Industrial Cooperation Corp, Seoul (KR)

(72) Inventors: Woo Yong Shim, Suwon-si (KR); Jung-kul Lee, Seoul (KR); Jae-Young Kim, Suwon-si (KR); Jinha Kim, Suwon-si (KR); Singh Bakul, Seoul (KR); Seung Hoon Song, Suwon-si (KR); Yu Kyung Jung, Suwon-si (KR); Kugalur Karuppanan Karthikeyan, Seoul (KR)

(73) Assignees: SAMSUNG ELECTRONICS CO., LTD., Gyeonggi-Do (KR); KONKUK UNIVERSITY INDUSTRIAL COOPERATION CORP, Seoul (KR)

( * ) Notice: Subject to any disclaimer, the term of this patent is extended or adjusted under 35 U.S.C. 154(b) by 271 days.

(21) Appl. No.: 18/607,662

(22) Filed: Mar. 18, 2024

(65) Prior Publication Data

US 2025/0051734 A1 Feb. 13, 2025

(30) Foreign Application Priority Data

Aug. 10, 2023 (KR) ........................ 10-2023-0105095
Nov. 27, 2023 (KR) ........................ 10-2023-0167157

(51) Int. Cl.

| | |
|---|---|
| ***C12N 9/06*** | (2006.01) |
| ***C01B 32/914*** | (2017.01) |
| ***C01G 39/00*** | (2006.01) |
| *B82Y 30/00* | (2011.01) |

(52) U.S. Cl.

CPC .......... *C12N 9/0046* (2013.01); *C01B 32/914* (2017.08); *C01G 39/006* (2013.01); *B82Y 30/00* (2013.01); *C01P 2004/20* (2013.01); *C01P 2006/40* (2013.01)

(58) Field of Classification Search

CPC ................................ C12N 9/0046; C12N 9/06
See application file for complete search history.

(56) References Cited

U.S. PATENT DOCUMENTS

2017/0088429 A1 3/2017 Shin et al.
2025/0051734 A1* 2/2025 Shim .................... C01B 32/914

FOREIGN PATENT DOCUMENTS

| | | | |
|---|---|---|---|
| CN | 112968188 | A | 6/2021 |
| CN | 108383098 | B | 1/2022 |
| KR | 20170036507 | A | 4/2017 |
| KR | 102402079 | B1 | 5/2022 |
| KR | 20220159775 | A | 12/2022 |

OTHER PUBLICATIONS

Aneesh Koyappayil et al, Aneesh Koyappayil et al., "β-Hydroxybutyrate dehydrogenase decorated MXene nanosheets for the amperometric determination of β-hydroxybutyrate", Microchimica Acta (2020) 187: 277.
Junmei Liang et al, Junmei Liang et al., "Heterostructure engineering of Co-doped MoS2 coupled with Mo2CTx MXene for enhanced hydrogen evolution in alkaline media", Nanoscale, 2019, 11, 10992.
Kang Rui Garrick Lim et al.,, Kang Rui Garrick Lim et al., "Rational Design of Two-Dimensional Transition Metal Carbide/Nitride (MXene) Hybrids and Nanocomposites for Catalytic Energy Storage and Conversion", Kang R.G. Lim 등, ACS Nano 2020, 14, 10834-10864.
Lingxia Wu et al.,, Lingxia Wu et al., "2D transition metal carbide MXene as a robust biosensing platform for enzyme immobilization and ultrasensitive detection of phenol", Biosensors and Bioelectronics, 107, 69-75. (2018).
R. B. Rakhi et al.,, R. B. Rakhi et al., "Novel amperometric glucose biosensor based on MXene nanocomposite", Scientific Reports, 6:36422. (2016).
Xianhong Wu et al.,, Xianhong Wu et al., "Engineering Multifunctional Collaborative Catalytic Interface Enabling Efficient Hydrogen Evolution in All pH Range and Seawater", Adv. Energy Mater. 2019, 1901333.
Yi Tang et al.,, Yi Tang et al., "Synergistically Coupling Phosphorus-Doped Molybdenum Carbide with MXene as a Highly Efficient and Stable Electrocatalyst for Hydrogen Evolution Reaction", ACS Sustainable Chem. Eng. 2020, 8, 12990-12998.

* cited by examiner

*Primary Examiner* — Tekchand Saidha
(74) *Attorney, Agent, or Firm* — CANTOR COLBURN LLP

(57) ABSTRACT

An MXene or a derivative thereof, on which nitrous oxide reductase is immobilized, wherein the MXene has a formula of $M_{n+1}X_nT_s$, wherein M is a transition metal of Groups 3, 4, 5, 6, or a combination thereof, of the Periodic Table of the Elements, X is carbon, nitrogen, or a combination thereof, T is oxide, epoxide, hydroxide, C1-C5 alkoxide, fluoride, chloride, bromide, iodide, or a combination thereof, and n is 1, 2, or 3, and s is 0, 1, or 2.

8 Claims, 26 Drawing Sheets

FIG. 3A1
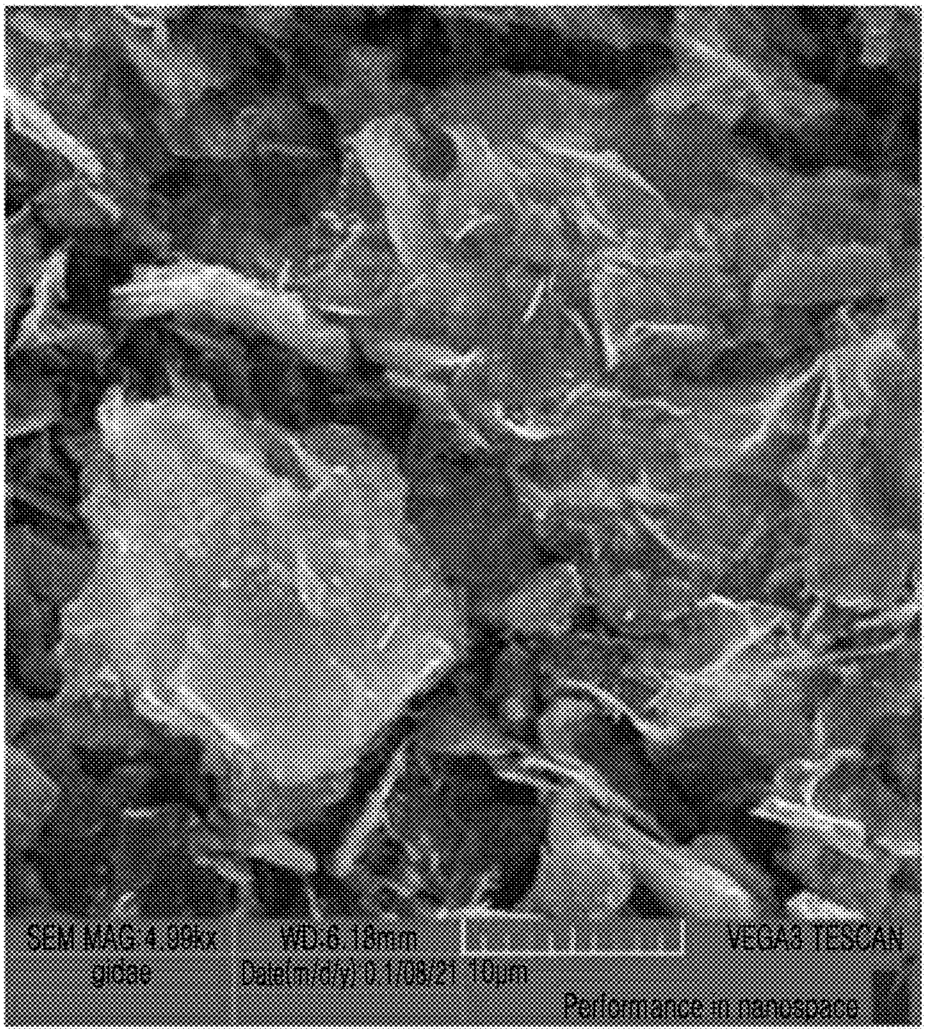

FIG. 3A2
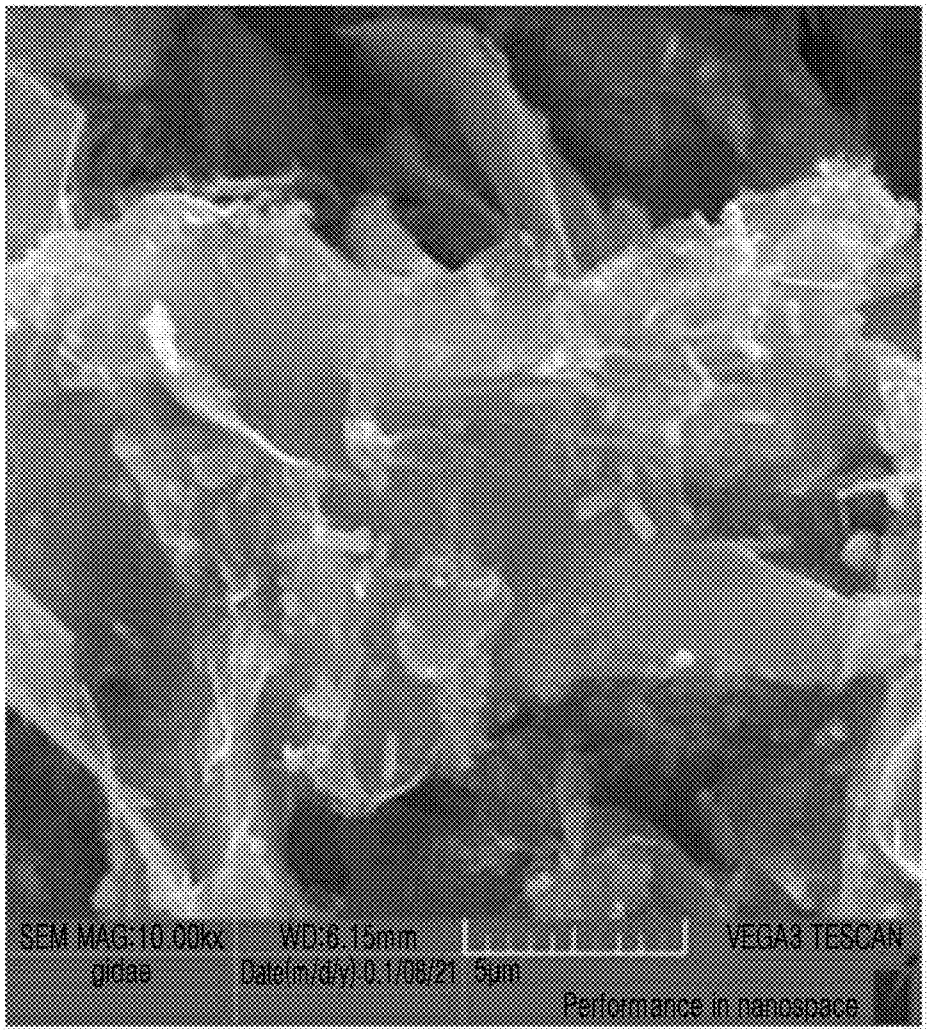

FIG. 3B1
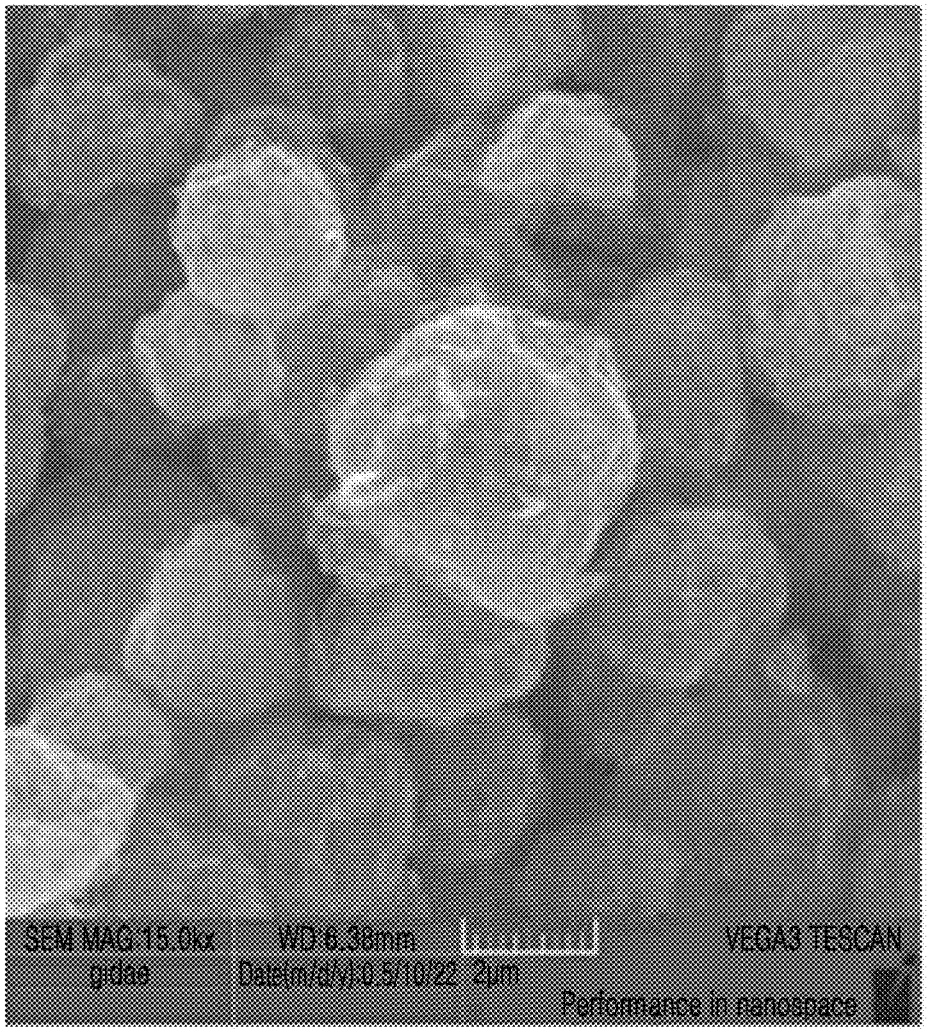

FIG. 3B2
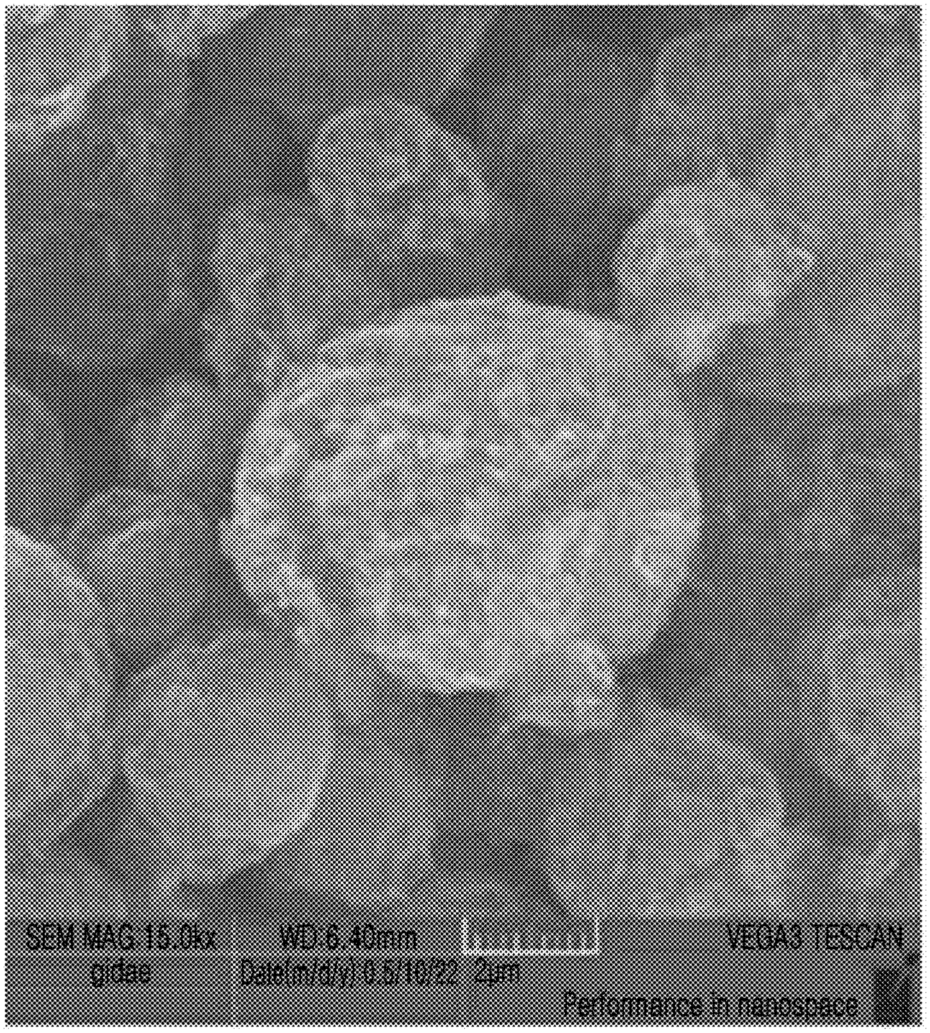

MXENE OR DERIVATIVE THEREOF IMMOBILIZED WITH NITROUS OXIDE REDUCTASE AND USE THEREOF

CROSS-REFERENCE TO RELATED APPLICATION

This application is based on and claims priority under 35 U.S.C. § 119 to Korean Patent Application No. 10-2023-0105095, filed on Aug. 10, 2023, and No. 10-2023-0167157, filed on Nov. 27, 2023, in the Korean Intellectual Property Office, the disclosure of which is incorporated by reference herein in its entirety.

BACKGROUND

1. Field

The disclosure relates to an MXene or a derivative thereof, on which nitrous oxide reductase is immobilized, and use thereof.

2. Description of the Related Art

Graphene is a single-atomic layer material consisting of carbon atoms in a honeycomb structure, and due to the excellent physical properties thereof, there has been significant interest in graphene. Extensive research on graphene has recently expanded interest into research on graphene-like two-dimensional materials.

As one of such two-dimensional materials, a delaminated material of a MAX phase has been introduced. The MAX phase (wherein M is a transition metal, A is an element of Group 13 or Group 14, and X is carbon and/or nitrogen) is a crystalline material consisting of a combination of MX having quasi-ceramic properties and A which is a different metal element from M, and the delaminated material of the MAX phase has excellent physical properties such as electrical conductivity, oxidation resistance, and machinability. To date, it is known that more than 60 types of MAX phase have been synthesized.

A MAX phase is a three-dimensional material, but unlike graphite or metal dichalcogenide materials, transition metal carbide layers are stacked with weak chemical bonds between the element A and the transition metal M. Therefore, it is difficult to transform a MAX phase into a two-dimensional structure using general mechanical or chemical delamination methods.

The MAX phase has been transformed into a two-dimensional structure having different properties from the MAX phase by selectively removing aluminum layers from the three-dimensional titanium-aluminum carbide of the MAX phase. The two-dimensional material includes "MXene." It is desired to utilize MXene and a derivative thereof due to MXene having similar electrical conductivity and strength to those of graphene.

SUMMARY

Provided is an MXene or a derivative thereof, on which nitrous oxide reductase (Nos) is immobilized, wherein the MXene has a formula of $M_{n+1}X_nT_s$, wherein M is a transition metal of Groups 3, 4, 5, 6, or a combination thereof, of the Periodic Table of the Elements, X is carbon (C), nitrogen (N), or a combination thereof, T is oxide (O), epoxide, hydroxide (OH), C1-C5 alkoxide, fluoride (F), chloride (Cl), bromide (Br), iodide (I), or a combination thereof, n is 1, 2, or 3, and s is 0, 1, or 2.

Provided is an electrode for use in reducing $N_2O$ to $N_2$, the electrode including the MXene or a derivative thereof, and Nos immobilized on the MXene or a derivative thereof.

Provided is an apparatus (e.g., device) for use in reducing $N_2O$ to $N_2$, the apparatus including the electrode.

In an aspect, provided is an apparatus for use in reducing $N_2O$ to $N_2$, the apparatus including a working electrode, a counter electrode, and a reference electrode, wherein the working electrode is the aforementioned electrode.

Provided is a method of reducing $N_2O$ to $N_2$, the method including: contacting the electrode with $N_2O$ or a dissolved form thereof in a liquid medium; and applying a current to the electrode.

Provided is a hybrid material (i.e., hybrid) of a transition metal carbide (TMC) comprising $Mo_2C$ or $W_2C$; and MXene or a derivative thereof, in which the TMC is bonded to the MXene, wherein the MXene has a formula (e.g., composition) of $M_{n+1}X_nT_s$, wherein M is a transition metal of Groups 3, 4, 5, 6, or a combination thereof, of the periodic table of the elements, X is carbon (C), nitrogen (N), or a combination thereof, T is oxide (O), epoxide, hydroxide (OH), C1-C5 alkoxide, fluoride (F), chloride (Cl), bromide (Br), iodide (I), or a combination thereof, n is 1, 2, or 3, and s is 0, 1, or 2. T may be a surface terminal group. The surface terminal group may be a negatively charged group, such as —O, and —OH.

Provided is a method of preparing a hybrid material of TMC and an MXene or a derivative thereof, in which the TMC is bonded to the MXene or a derivative thereof, the method including: annealing a mixture of MXene or a derivative thereof and a transition metal source compound at a temperature in a range of about 350° C. to about 600° C., and carbonizing the annealed product at a temperature in a range of about 750° C. to about 850° C. to prepare the hybrid material.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 3A1 and 3A2 show scanning electron microscopy (SEM) images of a two-dimensional (2D) $Mo_2C$@$Ti_3C_2$ MXene;

FIGS. 3B1 and 3B2 show SEM images of a 3D $Mo_2C$@$Ti_3C_2$ MXene;

DETAILED DESCRIPTION

Figure 1:
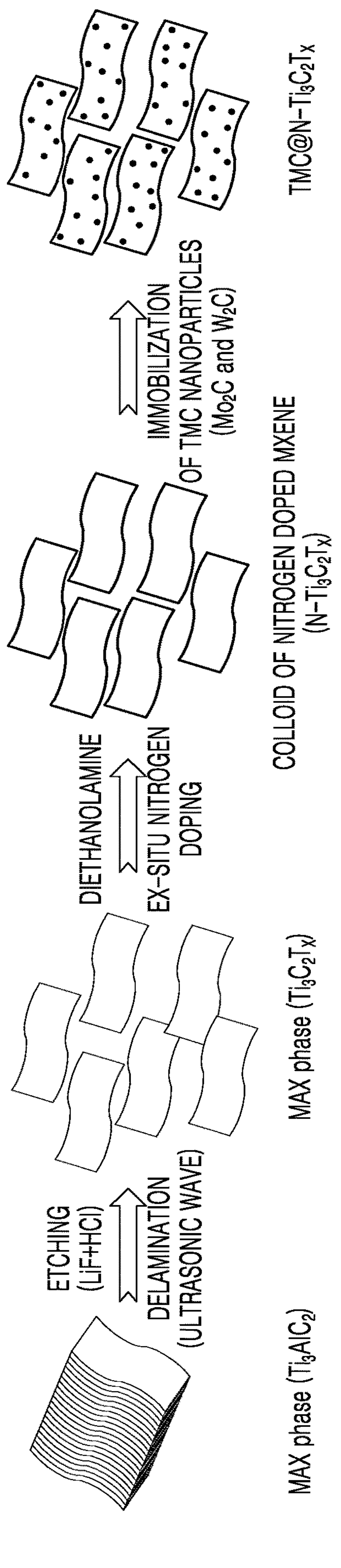
FIG. 1 is a diagram showing a process of preparing a hybrid of a transition metal carbide (TMC) and $Ti_3C_2$ MXene from a MAX phase.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figure, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a", "an," "the," and "at least one" do not denote a limitation of quantity, and are intended to include both the singular and plural, unless the context clearly indicates otherwise. For example, "an element" has the same meaning as "at least one element," unless the context clearly indicates otherwise. Thus, reference to "an" element in a claim followed by reference to "the" element is inclusive of one element and a plurality of the elements. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value. All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.).

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, the present disclosure will be described in detail with reference to Examples below. However, these Examples are for illustrative purposes only, and the scope of the present disclosure is not intended to be limited by these Examples.

A delaminated structure of a MAX phase has excellent physical properties such as electrical conductivity, oxidation resistance, and machinability, however, it is difficult to transform the MAX phase into a two-dimensional structure using general mechanical or chemical delamination methods.

Recently in 2011, a research team led by Professor Michel W. Barsoum at Drexel university succeeded in transforming a MAX phase into a two-dimensional structure with completely different properties using hydrofluoric acid to selectively remove aluminum layers from the three-dimensional titanium-aluminum carbide of the MAX phase. The research team names the two-dimensional material obtained by delaminating a MAX phase as "MXene". MXene has similar electrical conductivity and strength to those of graphene, and can be applied to a variety of application technologies ranging from energy storage devices to biomedical applications and composites.

Nonetheless, there is a need for new uses of MXene and a derivative thereof.

Disclosed is an MXene or a derivative thereof, on which nitrous oxide reductase is immobilized, wherein the MXene has a formula of $M_{n+1}X_nT_s$, wherein M is a transition metal of Groups 3, 4, 5, 6, or a combination thereof, of the Periodic Table of the Elements, X is carbon, nitrogen, or a combination thereof, T is oxide, epoxide, hydroxide, C1-C5 alkoxide, fluoride, chloride, bromide, iodide, or a combination thereof, n is 1, 2, or 3, and s is 0, 1, or 2.

Also disclosed is an electrode for use in reducing $N_2O$ to $N_2$, the electrode comprising the MXene or a derivative thereof, and nitrous oxide reductase immobilized on the MXene or a derivative thereof.

Also disclosed is an apparatus for use in reducing $N_2O$ to $N_2$, comprising the electrode.

Also disclosed is a method of reducing $N_2O$ to $N_2$, the method comprising: contacting $N_2O$ or a dissolved form thereof in a liquid medium with the electrode; and applying a current to the electrode.

Also disclosed is a hybrid material wherein the hybrid material comprises a transition metal carbide comprising $Mo_2C$ or $W_2C$; and an MXene or a derivative thereof, in which the transition metal carbide is bonded to the MXene or a derivative thereof, wherein the MXene has a composition of $M_{n+1}X_nT_s$, wherein M is a transition metal of Groups 3, 4, 5, 6, or a combination thereof, of the Periodic Table of the Elements, X is carbon, nitrogen, or a combination thereof, T is oxide, epoxide, hydroxide, C1-C5 alkoxide, fluoride, chloride, bromide, iodide, or a combination thereof, n is 1, 2, or 3, and s is 0, 1, or 2.

Also disclosed is a method of preparing a hybrid material of a transition metal carbide and an MXene or a derivative thereof, in which the transition metal carbide is bonded to the MXene or a derivative thereof, the method comprising:

annealing a mixture of the MXene or a derivative thereof and a transition metal source compound at a temperature in a range of about 350° C. to about 600° C. to produce an annealed product; and carbonizing the annealed product at a temperature in a range of about 750° C. to about 850° C. to prepare the hybrid material.

Additional aspects will be set forth in part in the description which follows and, in part, will be apparent from the description, or may be learned by practice of the presented embodiments of the disclosure.

In the present specification, the term "MXene" refers to a large class of two-dimensional (2D) material, which can be applied in various fields including electrochemical energy storage, electromagnetic interference shielding, gas sensing, antennas and radio frequency identification (RFID) tags, electrochromic devices, etc. The MXene may be represented by a general formula of $M_{n+1}X_nT_s$, wherein M may be, for example, an early transition metal (e.g., Sc, Ti, V, Cr, Zr, Nb, Mo, Hf, or Ta), X may be C and/or N, n may be 1, 2, or 3, and T may be a surface functional group such as —F, —OH, or —O.

The MXene may be prepared by selectively removing an A atomic layer from a $M_{n+1}AX_n$ phase material. The removing of the A atomic layer may be performed under acid conditions. The removing of the A atomic layer may be performed using a strong acid including a fluorine atom. The removing of the A atomic layer may be performed using hydrofluoric acid (HF), $LiHF_2$, $NaHF_2$, $KHF_2$, lithium fluoride (LiF), sodium fluoride (NaF), magnesium fluoride ($MgF_2$), strontium fluoride ($SrF_2$), beryllium fluoride ($BeF_2$), calcium fluoride ($CaF_2$), ammonium fluoride ($NH_4F$), ammonium difluoride ($NH_4HF_2$), ammonium hexafluoroaluminate ($(NH_4)_3AlF_6$), or a combination thereof, or one or more of a combination of the foregoing and one or more of hydrochloric acid, sulfuric acid, or nitric acid. The removing may be performed by an etching process. The removing of the A atomic layer may be performed at a temperature in a range of about 20° C. to about 800° C., about 50° C. to about 600° C., or about 100° C. to about 400° C. A in the MXene formula may include at least one of Groups 12, 13, 14, 15, 16 elements, or a combination thereof, of the Periodic Table of Elements. For example, A in the MXene formula may be Al, Si, P, S, or Ga. M in the MXene formula may be Sc, Y, Lu, Ti, Zr, Hf, V, Nb, Ta, Cr, Mo, or W.

The compound of the formula of $M_{n+1}AX_n$ may include $Ti_2CdC$, $Sc_2InC$, $Ti_2AlC$, $Ti_2GaC$, $Ti_2InC$, $Ti_2TlC$, $V_2AlC$, $V_2GaC$, $Cl_2GaC$, $Ti_2AlN$, $Ti_2GaN$, $Ti_2InN$, $V_2GaN$, $Cr_2GaN$, $Ti_2GeC$, $Ti_2SnC$, $Ti_2PbC$, $V_2GeC$, $Cr_2AlC$, $Cr_2GeC$, $V_2PC$, $V_2AsC$, $Ti_2SC$, $Zr_2InC$, $Zr_2TlC$, $Nb_2AlC$, $Nb_2GaC$, $Nb_2InC$, $Mo_2GaC$, $Zr_2InN$, $Zr_2TlN$, $Zr_2SnC$, $Zr_2PbC$, $Nb_2SnC$, $Nb_2PC$, $Nb_2AsC$, $Zr_2SC$, $Nb_2SC$, $Hf_2InC$, $Hf_2TlC$, $Ta_2AlC$, $Ta_2GaC$, $Hf_2SnC$, $Hf_2PbC$, $Hf_2SnN$, $Hf_2SC$; $Ti_3AlC_2$, $V_3AlC_2$, $Ti_3SiC_2$, $Ti_3GeC_2$, $Ti_3SnC_2$, $Ta_3AlC_2$; $Ti_4AlN_3$, $V_4AlC_3$, $Ti_4GaC_3$, $Ti_4SiC_3$, $Ti_4GeC_3$, $Nb_4AlC_3$, $Ta_4AlC_3$, or a combination thereof.

The formula of $M_{n+1}X_nT_s$ may be $M_{n+1}X_n(OH)_xO_yF_z$ (wherein x, y, and z are molar ratios of each functional group present on the surface per mole of $M_{n+1}X_n$).

The MXene may be in the form of nanosheets or flakes. The nanosheet may have a double-layer structure or a few-layer structure. In an aspect, the few-layer structure (e.g., few-layer nanosheets) may comprise 2 to 10, 2 to 7, 3 to 5, or 2, 3, 4, 5, 6, 7, 8, 9, or 10 interlaced layers.

An MXene phase material used to prepare the MXene may be also referred to as a MAX phase precursor. The MAX phase precursor may be, for example, $Ti_3AlC_2$. The $Ti_3AlC_2$ may be synthesized by, as a carbon source, any one of graphite, carbon lampblack, and titanium carbide (TIC).

The Nos may be an enzyme that catalyzes conversion of $N_2O$ to $N_2$ using $N_2O$ as a substrate. The Nos may be NosZ. NosZ is a product of a NosZ gene, and is an enzyme that catalyzes conversion of $N_2O$ to $N_2$. That is, NosZ may be Nos. NosZ may be a homodimeric metalloprotein of 130 kDa that contains two copper centers, CuA and CuZ, in each monomer. The Nos may have enzymatic activity of EC 1.7.2.4. The Nos may be natural or a variant including an amino acid residue mutation. The mutation may be, for example, a substitution of the amino acid residue. The Nos may be, for example, Nos derived from the genus *Pseudomonas* or the genus *Paracoccus*. A microorganism of the genus *Pseudomonas* may be *P. stutzeri* or *P. aeruginosa*. A microorganism of the genus *Paracoccus* may be *P. versutus*.

The derivative may be N-, P-, or S-doped MXene or a hybrid of MXene and TMC.

The N-, P-, or S-doped MXene may be prepared by a method including annealing a mixture of an N-, P-, or S-source compound and MXene. For example, N-doped $Ti_3C_2$ MXene may be prepared by mixing $Ti_3C_2$ MXene in a mixed solvent of diethanolamine and methanol as an N-source compound, and the annealing the resulting mixture at a temperature in a range of about 150° C. to about 250° C., about 170° C. to about 230° C., for example, about 180° C. The annealing may be performed for about 12 hours to about 36 hours, about 18 hours to about 30 hours, for example, about 24 hours.

The transition metal may be Sc, Y, Lu, Ti, Zr, Hf, V, Nb, Ta, Cr, Mo, W, or a combination thereof.

A hybrid of TMC and MXene may be prepared by a method of preparing a hybrid in which TMC is bonded to MXene the method including: annealing a mixture of MXene and a transition metal source compound at a temperature in a range of about 350° C. to about 600° C., about 400° C. to about 550° C., or about 450° C. to about 500° C., to produce an annealed product; and carbonizing the annealed product at a temperature in a range of about 750° C. to about 850° C., about 770° C. to about 830° C., or about 700° C. to about 800° C.

In the method, the annealing may be performed for about 10 minutes to about 2 hours, about 30 minutes to about 1.5 hours, or about 45 minutes to about 1.2 hours. In the method, the carbonizing may be performed for about 2 hours to about 8 hours, about 3 hours to about 7 hours, or about 4 hours to about 6 hours.

In the method, the MXene may be $Ti_3C_2$ MXene, and the TMC may be $Mo_2C$ or $W_2C$.

In the method, the transition metal source compound may be ammonium heptamolybdate ($(NH_4)$ $Mo_7O_{24}$-$4H_2O$) or ammonium metatungstate hydrate.

The derivative may be N-, P-, or S-doped $Ti_3C_2$ MXene, a $Mo_2C@Ti_3C_2$ MXene hybrid (i.e., a hybrid of $Mo_2C$ and $Ti_3C_2$), a $Mo_2C$@N-, P-, or S-doped $Ti_3C_2$ MXene hybrid (i.e., a hybrid of $Mo_2C$ and N-, P-, or S-doped $Ti_3C_2$), a $W_2C@Ti_3C_2$ MXene hybrid (i.e., a hybrid of $W_2C$ and $Ti_3C_2$), or a $W_2C$@N-, P-, or S-doped $Ti_3C_2$ MXene hybrid (i.e., a hybrid of $W_2C$ and N-, P-, or S-doped $Ti_3C_2$).

The MXene or a derivative thereof may have a three-dimensional structure. The three-dimensional structure refers to a spherical shape, for example, a downy-like fluffy shape. The three-dimensional structure refers to a fluffy shape in which TMC nanoparticles, i.e., $Mo_2C$ or $W_2C$ nanoparticles, are bonded to a $Ti_3C_2$ nanosheet, and a plurality of the $Ti_3C_2$ nanosheets bonded with the $Mo_2C$ or $W_2C$ nanoparticles are intertwined. Here, the three-dimensional structure may have an average diameter in a range of about 3 micrometers (μm) to about 4 μm, 3.2 μm to about 3.8 μm, or 3.4 μm to about 3.6 μm. Also, the three-dimensional structure may have a three-dimensional structure in which delaminated few-layer MXene nanosheets are cross-linked between layers (e.g., interlaced). The three-dimensional structure may have a porous structure, for example, a mesoporous structure.

The three-dimensional structure may be prepared by spraying a solution of nanosheet-shaped MXene or a derivative thereof having a two-layer or a few-layer or more layers (e.g., 11 to 50 layers) of nanosheet structure in the presence of ultrasonic waves to form aerosol droplets, and then by drying the formed aerosol droplets. For example, the three-dimensional structure may be prepared by adding each of the $Ti_3C_2$ nanosheet or N-, P-, or S-doped $Ti_3C_2$ nanosheet, the $W_2C@Ti_3C_2$ hybrid, the $W_2C$@N-, P-, or S-doped $Ti_3C_2$ hybrid, the $Mo_2C@Ti_3C_2$ hybrid, and the $Mo_2C$@N-, P-, or S-doped $Ti_3C_2$ hybrid to an aqueous solvent to obtain a colloidal solution, ultrasonically nebulizing the colloidal solution using a ultrasonic atomizer at a constant feeding rate to form aerosol droplets, and flowing the aerosol droplets through a tube furnace connected to the ultrasonic atomizer using argon as a carrier gas. The tube furnace may be pre-heated to a temperature in a range of about 550° C. to about 650° C. before aerosolization. The resulting three-dimensional structure may be harvested by an electrostatic collector positioned at the end of the tube furnace.

The Nos may be immobilized on the MXene or a derivative thereof according to any suitable known method. The immobilization may be performed by physical or chemical methods. Physical methods may include adsorption or entrapment. The adsorption may be achieved through van der Waals forces or non-specific forces such as hydrogen and hydrophobic interactions. Chemical methods may include cross-linking or covalent bonding. The crossing may be covalent bonding among enzymes at a site other than the active site of the enzyme. The covalent bond may refer to covalent bonding of enzymes to an insoluble support such as silica gel or a macroporous polymer bead. The immobilization may be achieved through an affinity-tag.

The immobilized silanized surface may be cross-linked with a carbon compound having two or more formyl groups.

The silanization may refer to functionalizing the surface with alkoxysilane. The alkoxysilane may be (aminoalkyl) trialkoxysilane. The aminoalkyl group and the trialkoxy group may each have any carbon length, for example, 2 to 50 carbons, 2 to 30 carbons, 2 to 20 carbons, 3 to 50 carbons, 3 to 30 carbons, 3 to 20 carbons, 5 to 50 carbons, 5 to 30 carbons, or 5 to 20 carbons. The (aminoalkyl)trialkoxysilane may be, for example, APTES. The APTES may be an aminosilane frequently used for silanization.

The carbon compound having two or more formyl groups may refer to a material having formyl groups at both ends and having any carbon length, for example, 2 to 50 carbons, 2 to 30 carbons, 2 to 20 carbons, 3 to 50 carbons, 3 to 30 carbons, 3 to 20 carbons, 5 to 50 carbons, 5 to 30 carbons, or 5 to 20 carbons. The carbon compound having two or more formyl groups may be glutaraldehyde. The glutaraldehyde may be a molecule consisting of a 5-carbon chain with formyl groups at both ends. The glutaraldehyde may have two carbonyl groups that are reactive with primary amine groups or hydrates thereof, and thus may act as a cross-linking agent for materials with primary amine groups, thereby forming imine-connected links.

According to another aspect of the disclosure, provided is an electrode for use in reducing $N_2O$ to $N_2$, the electrode having immobilized thereon the MXene or a derivative thereof on which Nos is immobilized.

The expression "MXene or a derivative thereof on which Nos is immobilized" may be the same as described herein.

The electrode may be formed of any suitable material that allows current to flow. The electrode may be, for example, a glassy carbon electrode. When a current is applied, the electrode may promote reduction of $N_2O$ to $N_2$ by promoting current transfer to the Nos. The promotion may be achieved directly or through a mediator. The mediator may be benzyl viologen (BV).

In the electrode, the MXene or a derivative thereof may be immobilized by any suitable known method. The immobilization may be achieved by coating, deposition, or adhesion. The MXene or a derivative thereof may be immobilized on a surface of the electrode through a binder.

The immobilization may be achieved by, for example, drop casting or spin coating. The drop casting may include dropping a binder-containing solution onto a support surface. The Nos enzyme is coated on the surface together with the binder-containing solution, and may be deposited after the binding coating. The binder may be Nafion™, N-dodecyl-N,N-dimethyl-1-dodecanaminium bromide (DDAB), tetrabutylammonium bromide (TBAB), or a combination thereof.

According to another aspect of the disclosure, provided is a device (e.g., apparatus) for use in reducing $N_2O$ to $N_2$, the device including the electrode.

The device may include a working electrode, a counter electrode, and a reference electrode, wherein the working electrode is an electrode for use in reducing $N_2O$ to $N_2$ and has immobilized thereon the MXene or a derivative thereof on which Nos is immobilized.

The apparatus may include reagents, such as liquid media, cofactors, electron donors or acceptors, etc., necessary to perform an electroenzyme reaction. The device may be a chamber including the electrode according to an aspect and having an anaerobic atmosphere. The apparatus or chamber may include BV as an electron transfer mediator.

When a current is applied, the electrode according to an aspect may promote reduction of $N_2O$ to $N_2$ by promoting current transfer to the Nos. The promotion may be achieved directly or through a mediator. The mediator may be BV.

According to another aspect of the disclosure, provided is a method of reducing $N_2O$ to $N_2$, the method including: contacting the electrode according to an aspect with $N_2O$ or a dissolved form thereof in a liquid medium; and applying a current to the electrode.

The liquid medium may include any suitable material that assists catalyzing an enzyme reaction by Nos to reduce $N_2O$ to $N_2$. The liquid medium may be a buffer, for example, a phosphate buffer.

The dissolved form of $N_2O$ may be in the form of Fe(II)(L)-NO. The Fe(II)(L)-NO may represent that L, which is a chelating agent, $Fe^{2+}$, and NO are chelated to form a complex. L may be, for example, ethylenediamine, diethylenetriamine, triethylenetetramine, hexamethylenetetramine, N-(2-hydroxyethyl)ethylenediamine-triacetic acid (HEDTA), ethylenediamine-tetraacetic acid (EDTA), iminodiacetic acid, nitrilo-triacetic acid (NTA), or diethylenetriaminepentaacetic acid (DTPA). Accordingly, the Fe(II)(L)-NO may be in a form modified such that nitrogen oxides such as $N_2O$, NO, $N_2O_3$, $NO_2$, $N_2O_4$, and $N_2O_5$ are soluble in an aqueous solution. The Fe(II)(L)-NO may be formed by contacting nitrogen oxides with an aqueous solution containing Fe(II)(L). The contacting may include mixing an aqueous medium with liquid nitrogen oxides or contacting an aqueous medium with gaseous nitrogen oxides.

The contacting may be performed within the device. The contacting may be performed under anaerobic conditions.

According to another aspect of the disclosure, provided is a hybrid of TMC and MXene or a derivative thereof, in which the TMC is bonded to the MXene or a derivative thereof, wherein the MXene has a formula of $M_{n+1}X_nT_s$, wherein M may be a transition metal of Groups 3, 4, 5, 6, or a combination thereof, of the periodic table of the elements, X may be carbon (C), nitrogen (N), or a combination thereof, T may be oxide (O), epoxide, hydroxide (OH), C1-C5 alkoxide, fluoride (F), chloride (Cl), bromide (Br), iodide (I), or a combination thereof, n may be 1, 2, or 3, and s may be 0, 1, or 2. The TMC hybrid may be $Mo_2C$ or $W_2C$.

The derivative may be N-, P-, or S-doped MXene, or N-, P-, or S-doped $Ti_3C_2$ MXene.

The MXene may be $Ti_3C_2$ MXene.

According to another aspect of the disclosure, a method of preparing a hybrid in which TMC is bonded to MXene or a derivative thereof includes: annealing a mixture of MXene or a derivative thereof and a transition metal source compound at a temperature in a range of about 350° C. to about 600° C. to produce an annealed product, and carbonizing the annealed product at a temperature in a range of about 750° C. to about 850° C. to prepare the hybrid material.

In the method, the annealing may be performed for about 10 minutes to about 2 hours. In the method, the carbonizing may be performed for about 2 hours to about 8 hours.

In the method, the MXene may be $Ti_3C_2$ MXene, and the TMC may be $Mo_2C$ or $W_2C$.

In the method, the transition metal source compound may be ammonium heptamolybdate ($(NH_4)$ $Mo_7O_{24}$-$4H_2O$) or ammonium metatungstate hydrate.

The MXene or a derivative thereof on which Nos is immobilized according to an aspect may be used in the electrode or the device including the same for reducing $N_2O$ to $N_2$.

The electrode having immobilized thereon the MXene or a derivative on which Nos is immobilized according to an aspect may be efficiently used to reduce $N_2O$ to $N_2$.

The device including the electrode according to an aspect may be efficiently used to reduce $N_2O$ to $N_2$.

According to the method of reducing $N_2O$ to $N_2$ according to an aspect, $N_2O$ may be efficiency reduced to $N_2$.

The hybrid of TMC and MXene (i.e., TMC/MXene hybrid) according to an aspect in which TMC is bonded to MXene may be used as a support for immobilizing an enzyme such as Nos.

According to the method of preparing the TMC/MXene hybrid in which TMC is bonded to MXene according to an aspect, the TMC/MXene hybrid may be efficiently prepared.

Example 1: Preparation of Transition Metal Carbide/MXene Hybrid

In this Example, N-doped MXene was synthesized first, and then was bonded to and encapsulated by a transition metal carbide (TMC) to prepare a TMC/N-doped MXene hybrid.

(1.1) Synthesis of $Ti_3C_2$ MXene from MAX Phase $Ti_3C_2T_x$ MXene was prepared from a MAX phase precursor. $Ti_3AlC_2$ powder was used as the MAX phase precursor, and the prepared $Ti_3C_2T_x$ MXene was $Ti_3C_2T_x$ (hereinafter also referred to as "$Ti_3AlC_2$"). Here, $T_x$ is O, —OH, and/or F.

The $Ti_3AlC_2$ powder was purchased from Sigma-Aldrich Company. The $Ti_3AlC_2$ powder was converted to $Ti_3C_2T_x$ MXene and delaminated.

In detail, 2 grams (g) of $Ti_3AlC_2$ MAX phase powder was slowly added to an etching solution containing 1.6 g of LiF (99%) in 20 milliliters (mL) of 9 molar (M) HCl. Etching was performed thereon by stirring the reaction solution at 50° C. for 30 hours. Al was removed from $Ti_3AlC_2$ by the etching, and $Ti_3C_2$ MXene was formed. The resulting $Ti_3C_2$ MXene was almost universally terminated with —O, —OH, and/or —F after being etched, while not wishing to be bound by theory, which serves as a key factor in determining MXene behavior. Accordingly, MXene is also called $M_{n+1}X_nT_x$ as an extended name, or $M_{n+1}X_n$ for short.

Resulting dispersions were washed with deionized (DI) water and centrifuged at 3,500 rotations per minute (rpm) for 5 minutes each time. The supernatant was decanted, and remaining MXene was re-dispersed by shaking. This washing process was repeated until the pH of the mixture reached approximately 6 and self-delamination of the MXene occurred. The colloidal solution, which is the supernatant collected by centrifugation, was centrifuged at 1,500 rpm for 30 minutes to collect the precipitate containing the colloidal solution of delaminated $Ti_3C_2T_x$. The dark green supernatant thus obtained was further centrifuged at 4,500 rpm for 20 minutes to obtain the precipitate containing large-sized MXene flakes. To produce small-sized MXene flakes, the obtained 'precipitate' containing large-sized MXene was dispersed, and the resulting MXene dispersions were sonicated. The sonication was probe-sonicated in an ice bath for 20 minutes at an amplitude of 50% with 8 second on/2 second off pulses.

The resulting dispersions as a result of the sonication were centrifuged at 4,500 rpm for 20 minutes, and the supernatant was collected. Finally, a colloidal supernatant containing delaminated $Ti_3C_2T_x$ nanosheet was obtained. After the aforementioned washing process was completed, the MXene was dried in a vacuum environment at 60° C. for 24 hours to obtain a required $Ti_3C_2$ MXene film. The product thus obtained is also called FL-$Ti_3C_2$.

(1.2) Preparation of N-Doped $Ti_3C_2$ MXene Using Diethanolamine as Nitrogen Source Absolute ethanol was used to collect few-layer $Ti_3C_2$ (hereinafter also referred to as FL-$Ti_3C_2$) flakes. Ethanol was added at a volume ratio of at least 1:2 to $Ti_3C_2$ suspension (15 mL) contained in a 50 mL centrifuge tube.

The mixture was shaken and rotated for 3 minutes, and centrifuged at 9,000 rpm for 5 minutes. The precipitate was collected to obtain wet FL-$Ti_3C_2$ flakes. Diethanolamine was selected as a main nitrogen source and methanol as an auxiliary organic solvent, and these two solvents were mixed at a volume ratio of 1:1 (20 mL) to obtain a solvent mixture. The resulting solvent mixture was added to the FL-$Ti_3C_2$ precipitate accumulated in a centrifuge tube (50 mL), and the resulting reaction mixture in the centrifuge tube was shaken and rotated for 5 minutes. The reaction mixture in the centrifuge tube was sonicated at room temperature for 30 minutes, transferred to a Teflon container (50 mL), and then stirred for 30 minutes.

Afterwards, a stainless steel autoclave tank reactor with the Teflon container (50 mL) was treated in a drying oven at 180° C. for 24 hours to produce crude N-doped FL-$Ti_3C_2$ MXene.

After cooling, the solid residues were washed with alcohol (3 cycles) and ultrapure water (3 cycles), and centrifuged. After the last centrifugation, 30 mL of ultrapure water was added to the precipitate of N-doped FL-$Ti_3C_2$ flakes and the resulting mixture in the centrifuge tube was shaken and rotated for 5 minutes. The product thus obtained was sonicated for 1 hour, and a portion of the liquid supernatant was vacuum filtered and dried in the air at room temperature to obtain N-doped FL-$Ti_3C_2$ MXene.

(1.3) Immobilization of $Mo_2C$ and $W_2C$ Nanoparticles on MXene (1.3.1) Preparation of $Mo_2C/Ti_3C_2$ Hybrid (Hereinafter Referred to as "$Mo_2C@Ti_3C_2$ Hybrid")

1 g of ammonium heptamolybdate ($(NH_4)_6Mo_7O_{24}$-$4H_2O$) and 0.6 g of the synthesized N—$Ti_3C_2$ MXene were dispersed in a beaker containing 50 mL of ethanol.

The mixture was evaporated at 80° C. with vigorous stirring until ethanol was completely dried to provide a first product, and then the first product was transferred to an oven and kept at 60° C. for 6 hours. As a result, a dried product of dispersion of the ammonium heptamolybdate ($(NH_4)_6Mo_7O_{24}$-$4H_2O$) and the N-doped $Ti_3C_2$ MXene was obtained.

Lastly, the dried product was ground to obtain powder. This powder was used as a precursor for the preparation of a hybrid of $Mo_2C$ and $Ti_3C_2$, i.e., $Mo_2C/Ti_3C_2$ hybrid, or $Mo_2C@Ti_3C_2$.

The precursor was first heated in a tube furnace at a heating rate of 10° C./min, and then annealed at 550° C. for 1 hour. As a result, molybdenum oxide was obtained as a product of the annealing, which was then carbonized in an $H_2$/Ar gas mixture (containing 10% $H_2$) at 800° C. for 3 hours to produce a product in the furnace (hereinafter also referred to as "$Mo_2C@N$—$Ti_3C_2$ hybrid" or a hybrid of $Mo_2C$ and N—$Ti_3C_2$). Afterwards, the product in the furnace was cooled to room temperature.

In the obtained $Mo_2C@N$—$Ti_3C_2$ hybrid, the $Mo_2C$ was not trapped in the N-doped carbon (NC), but was directly bonded to the N—$Ti_3C_2$.

In the obtained $Mo_2C@N$—$Ti_3C_2$ hybrid, the carbon of the $Mo_2C$ was considered to be generated from the N—$Ti_3C_2$ MXene at a high temperature. The $Mo_2C@N$—$Ti_3C_2$ hybrid is considered to be formed by ionic and electrostatic interactions between the negatively charged MXene surface and the positively charged secondary material metal precursor. Due to these interactions, the adsorption occurred initially on the MXene and the secondary material metal precursor, and then, the secondary material was formed on the MXene surface through chemical treatment by heat treatment.

(1.3.2) Preparation of $W_2C/Ti_3C_2$ Hybrid (Hereinafter Referred to as "$W_2C@Ti_3C_2$ Hybrid")

1.478 g of ammonium metatungstate hydrate ($(NH_4)_6H_2W_{12}O_4$-$xH_2O$) and 0.2 g of N—$Ti_3C_2$ MXene were dissolved in DI water (500 mL) at room temperature. The resulting solution was stirred vigorously for 12 hours to recrystallize the ammonium metatungstate hydrate. This recrystallization process was performed for proper mixing of the ammonium metatungstate and the N—$Ti_3C_2$ MXene.

Next, the recrystallized solution was sonicated for 1 hour to obtain a homogeneous suspension. The homogeneous suspension thus obtained was evaporated at 180° C. under vacuum to collect crystalline solids. As a result, powder of the collected crystalline solids was used as a precursor for the preparation of a $W_2C/Ti_3C_2$ hybrid, i.e., a hybrid of $W_2C$ and $Ti_3C_2$.

First, the powder was heated up to 400° C. in a tube furnace at a heating rate of 2° C./min, and then annealed at 400° C. for 30 minutes. As a result, tungsten oxide was obtained as a product of the annealing which was then heated up to 800° C. at a heating rate of 5° C./min and carbonized at 800° C. for 5 hours under Ar gas (100 standard cubic centimeter per minute, sccm) to produce a product in the tube furnace (hereinafter referred to as "$W_2C$@N—$Ti_3C_2$ hybrid" or a hybrid of $W_2C$ and N—$Ti_3C_2$).

In the obtained $W_2C$@N—$Ti_3C_2$ hybrid, the $W_2C$ was not trapped in the N-doped carbon (NC), but was directly bonded to the N—$Ti_3C_2$.

In the obtained $W_2C$@N—$Ti_3C_2$ hybrid, the carbon of the $W_2C$ was considered to be generated from the $Ti_3C_2$ MXene at a high temperature. The $W_2C$@N—$Ti_3C_2$ hybrid is considered to be formed by ionic and electrostatic interactions between the negatively charged MXene surface and the positively charged secondary material metal precursor. Due to these interactions, the adsorption occurred initially on the MXene and the secondary material metal precursor, and then, the secondary material was formed on the MXene surface through chemical treatment by heat treatment. Afterwards, the product in the furnace was cooled to room temperature.

(1.3.3) Formation of Three-Dimensional Structure of $W_2C$@$Ti_3C_2$ Hybrid or $Mo_2C$@$Ti_3C_2$ Hybrid The $W_2C$@$Ti_3C_2$ hybrid and $Mo_2C$@$Ti_3C_2$ hybrid prepared in (1.3.1) and (1.3.2), respectively, each formed a three-dimensional structure.

In detail, the prepared $W_2C$@$Ti_3C_2$ hybrid and $Mo_2C$@$Ti_3C_2$ hybrid were each added at a concentration of 5 milligrams per milliliter (mg/mL) in DI water to obtain a colloidal solution.

The colloidal solution was ultrasonically nebulized through an ultrasonic atomizer at a feeding rate of 20 milliliters per hour (mL/h) to form aerosol droplets. The aerosol droplets thus obtained were then flowed through a tube furnace connected to the ultrasonic atomizer using argon as a carrier gas. Here, the tube furnace was pre-heated at 600° C. before the aerosolization. A product of the aerosolization was harvested by an electrostatic collector positioned at the end of the tube furnace.

The obtained $W_2C$@$Ti_3C_2$ hybrid and $Mo_2C$@$Ti_3C_2$ hybrid each had a three-dimensional structure. The three-dimensional structure refers to a spherical shape, for example, a downy-like fluffy shape. The three-dimensional structure refers to a fluffy shape in which transition metal carbide nanoparticles, i.e., $Mo_2C$ nanoparticles or $W_2C$ nanoparticles, are bonded to $Ti_3C_2$ nanosheets, and a plurality of the $Ti_3C_2$ nanosheets bonded with the $Mo_2C$ nanoparticles or $W_2C$ nanoparticles were intertwined (e.g., interlaced). Here, the three-dimensional structure had an average diameter in a range of about 3 micrometers (μm) to about 4 μm. The three-dimensional structure may have a porous structure such as a mesoporous structure.

Hereinafter, the $Mo_2C$@$Ti_3C_2$ hybrid and $W_2C$@$Ti_3C_2$ hybrid prepared in (1.3.1) and (1.3.2) will be also referred to as 2D $Mo_2C$@$Ti_3C_2$ and 2D $W_2C$@$Ti_3C_2$, respectively, the $Mo_2C$@$Ti_3C_2$ hybrid and $W_2C$@$Ti_3C_2$ hybrid prepared in (1.3.3) will be also referred to as 3D $Mo_2C$@$Ti_3C_2$ and 3D $W_2C$@$Ti_3C_2$, respectively.

FIG. 1 is a diagram showing the process of preparing a TMC/$Ti_3C_2$ MXene hybrid from a MAX phase. Here, TMC was $Mo_2C$ and $W_2C$, and MXene was N-doped $Ti_3C_2$ MXene. As shown in FIG. 1, the MAX phase was etched under strong acid to remove Al, thereby forming MXene. The resulting MXene was delaminated by sonication, thereby obtaining a single-layer MXene or a few-layer (FL)-MXene. In an aspect, the few-layer MXene comprises 2 to 10 layers. The resulting single-layer MXene or FL-MXene was mixed with diethanolamine, and the mixture was heat-treated at 180° C. to be ex-situ N-doped. The resulting N-doped MXene was mixed with a Mo-containing precursor, e.g., ammonium heptamolybdate ($(NH_4)_6Mo_7O_{24}$-$4H_2O$), as a Mo source and a W-containing precursor, e.g., ammonium metatungstate hydrate ($(NH_4)_6H_2W_{12}O_4$-$xH_2O$), as a W source to obtain a mixture precursor. The mixture precursor was then annealed and carbonized, thereby obtaining a TMC/N—$Ti_3C_2$ MXene hybrid (i.e., TMC/N-doped $Ti_3C_2$ MXene hybrid) on which the TMC was immobilized. Here, the annealing and carbonization were performed at 550° C. and 550° C., respectively.

Figure 2:
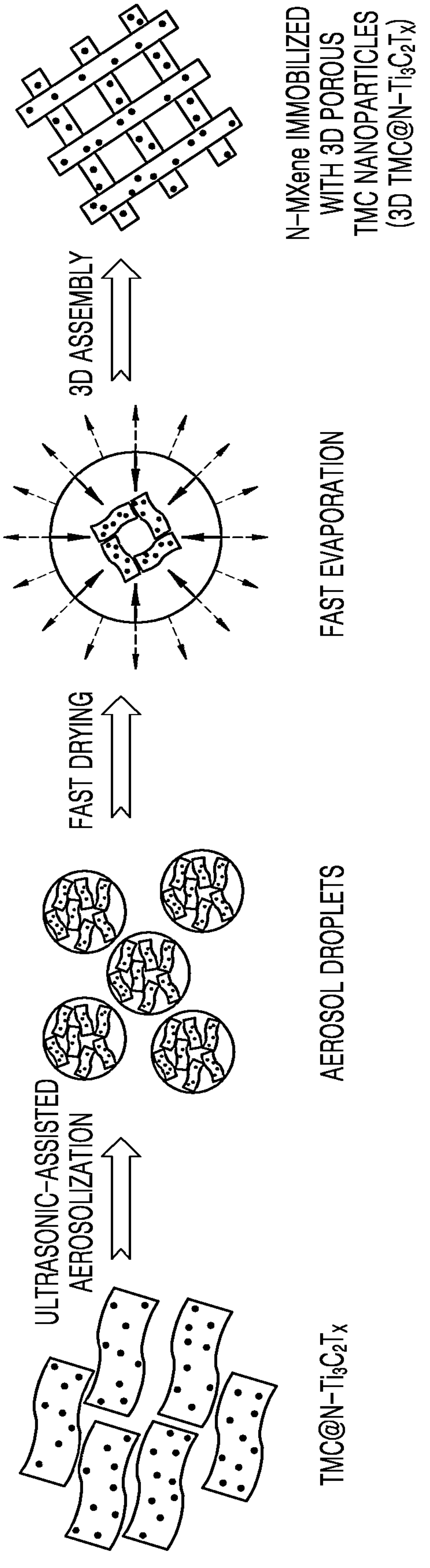
FIG. 2 is a diagram showing a process of converting a hybrid of a TMC and a N—$Ti_3C_2$, i.e., TMC@N-doped $Ti_3C_2$ MXene hybrid, into a three-dimensional (3D) structure.
Figure 4A:
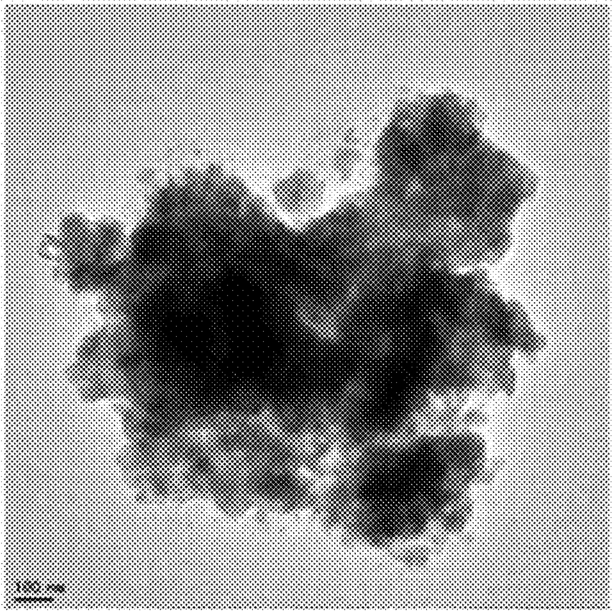
FIGS. 4A to 4D show transmission electron microscopy (TEM) images of a 2D $Mo_2C$@$Ti_3C_2$ MXene.
Figure 4B:
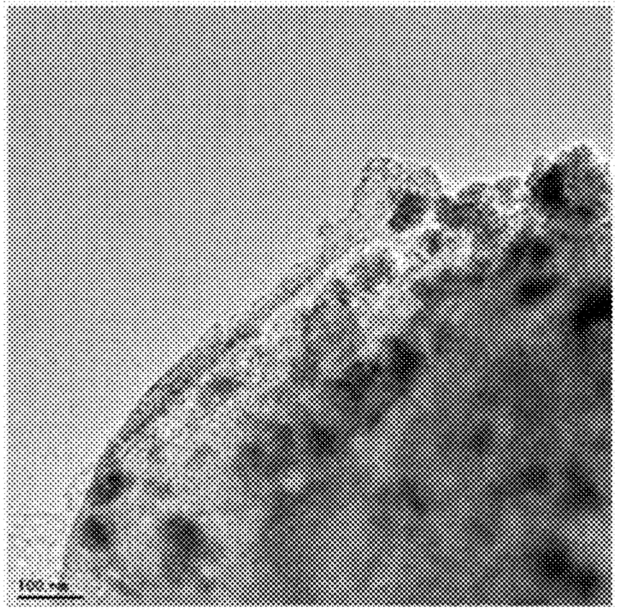
Figure 4C:
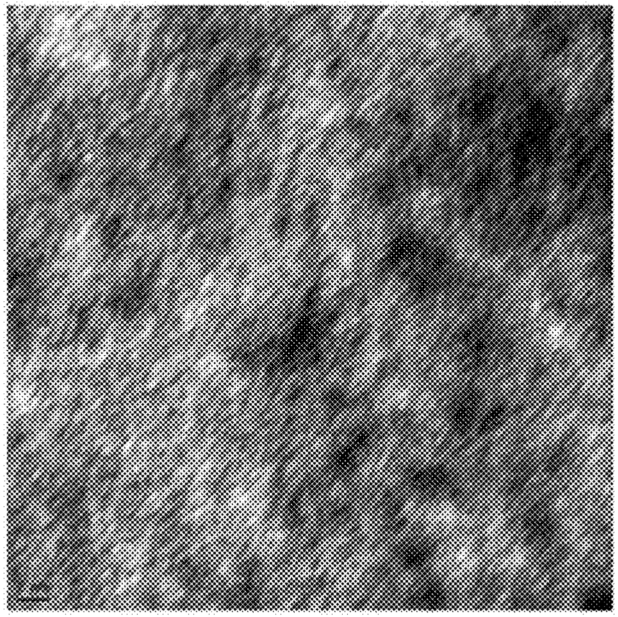
Figure 4D:
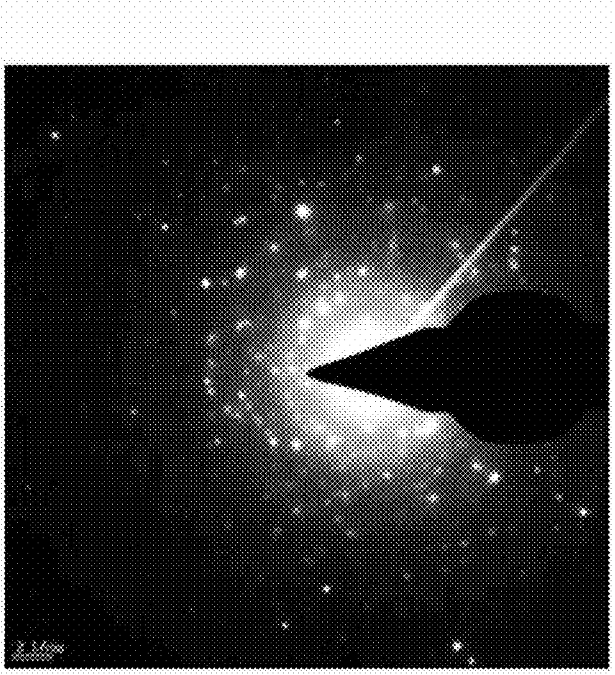
Figure 5A:
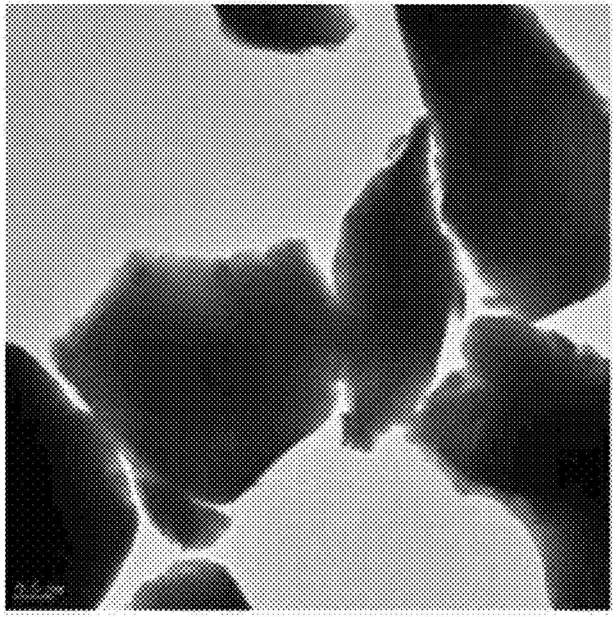
FIGS. 5A to 5D show transmission electron microscope (TEM) images of a commercially available 2D $Mo_2C$.
Figure 5B:
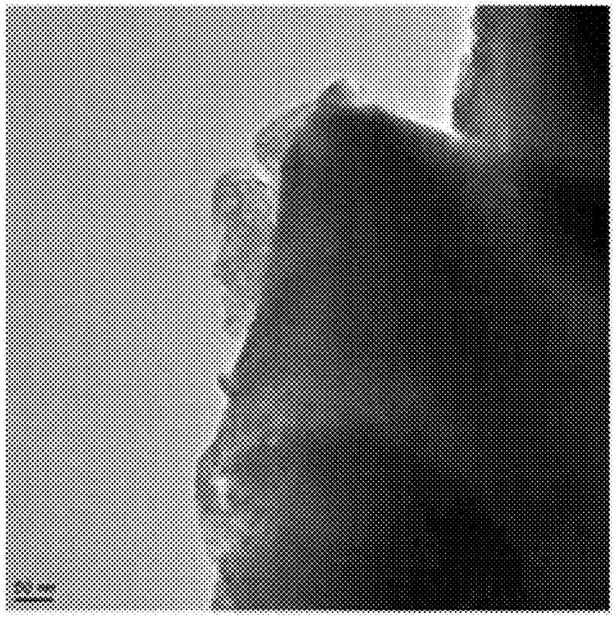
Figure 5C:
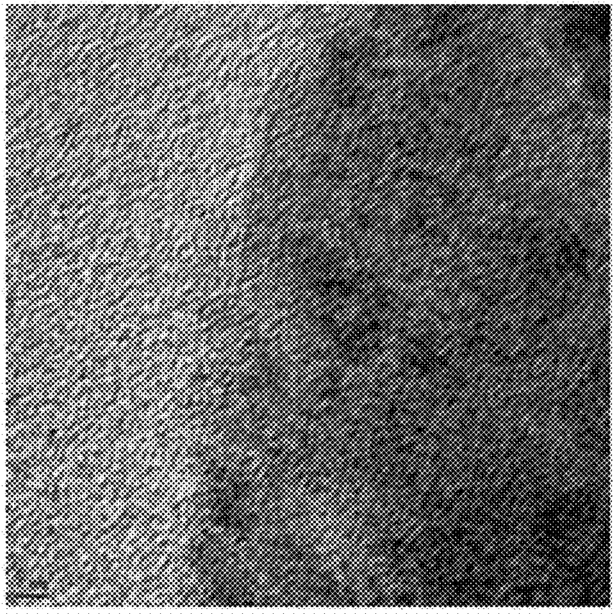
Figure 5D:
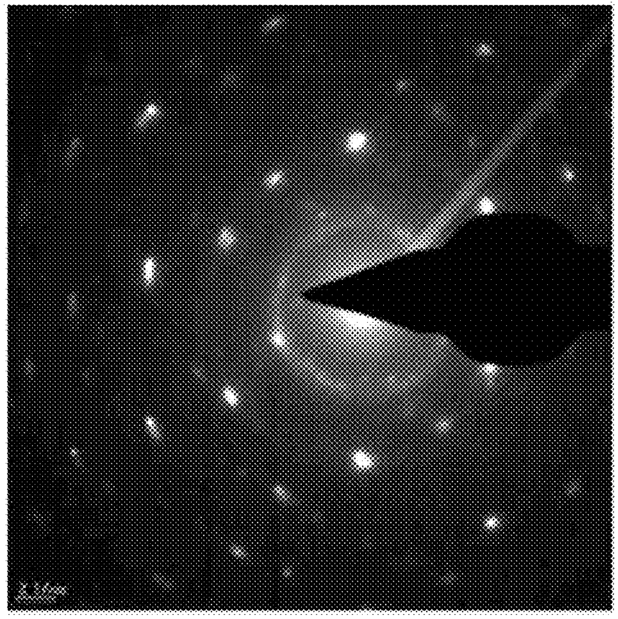

FIG. 2 is a diagram showing the process of converting the hybrid of TMC and N—$Ti_3C_2$ MXene, i.e., TMC@N—$Ti_3C_2$ MXene, into a three-dimensional structure. As shown in FIG. 2, a colloid of the TMC@N—$Ti_3C_2$ MXene hybrid was ultrasonically nebulized to obtain aerosol droplets. The resulting aerosol droplets were then quickly dried to allow three-dimensional assembly of TMC@N—$Ti_3C_2$ MXene nanosheets. Here, the three-dimensional assembly was achieved by capillary force. The inward capillary forces on the TMC@N—$Ti_3C_2$ MXene result in isotropic compression (solid arrow) and rapid assembly of the MXene nanosheets into the three-dimensional structure.

FIGS. 3A1 to 3B2 show scanning electron microscopy (SEM) images of a 2D $Mo_2C$@$Ti_3C_2$ and a 3D $Mo_2C$@$Ti_3C_2$. FIGS. 3A1 and 3A2 show the SEM images of the 2D $Mo_2C$@$Ti_3C_2$, and FIGS. 3B1 and 3B2 show the SEM images of the 3D $Mo_2C$@$Ti_3C_2$. As shown in FIGS. 3A1 to 3B2, the 2D $Mo_2C$@$Ti_3C_2$ of FIGS. 3A1 and 3A2 has a sheet-like shape, and the 3D $Mo_2C$@$Ti_3C_2$ of FIGS. 3B1 and 3B2 has a spherical shape.

FIGS. 4A-4D show transmission electron microscopy (TEM) images of a 2D $Mo_2C$@$Ti_3C_2$.

FIGS. 5A-5D show TEM images of a commercially available 2D $Mo_2C$ (by Sigma-Aldrich).

Figure 6A:
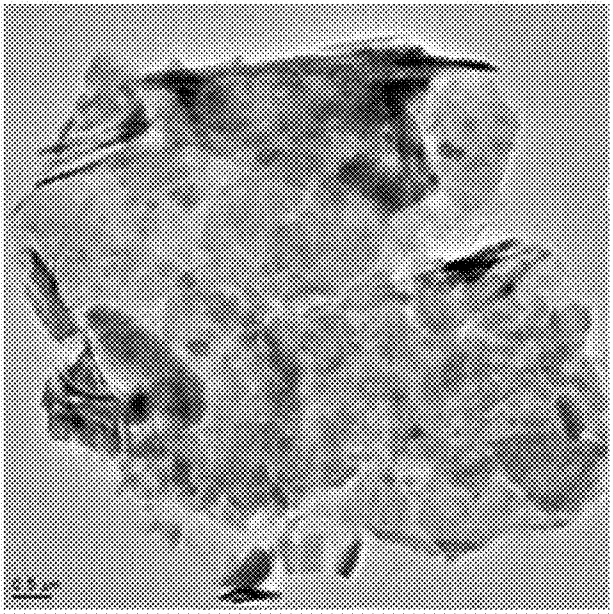
FIGS. 6A to 6D show TEM images of an N-doped $Ti_3C_2$ MXene.
Figure 6B:
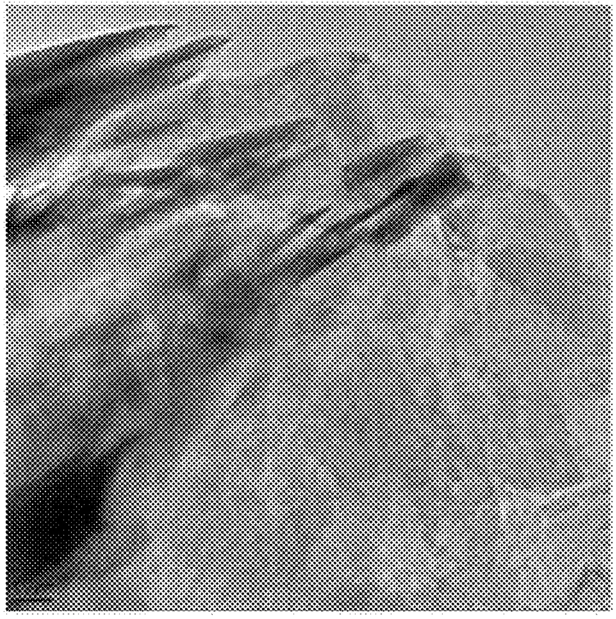
Figure 6C:
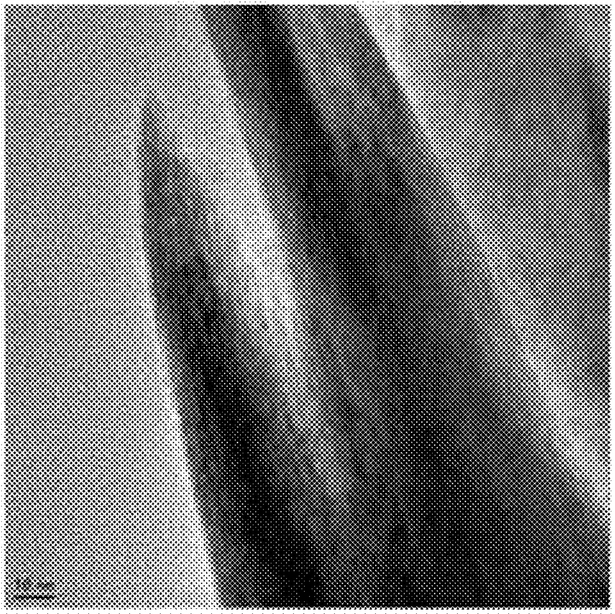
Figure 6D:
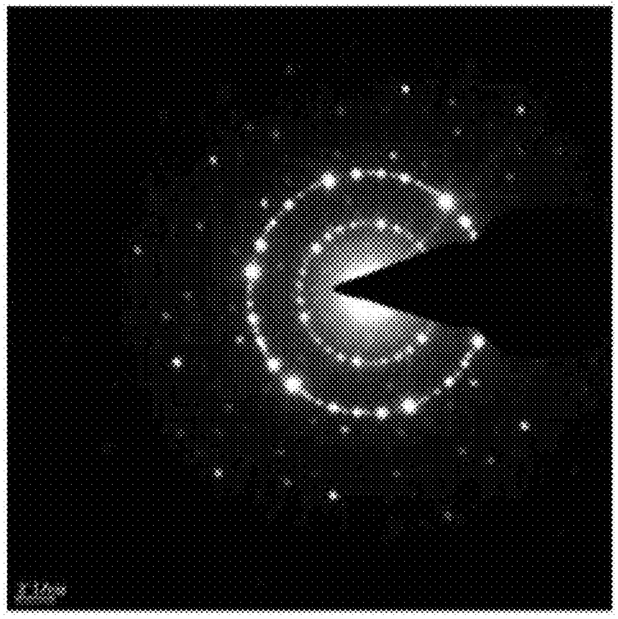

FIGS. 6A-6D show TEM images of an N-doped $Ti_3C_2$ MXene. In FIGS. 6A-6C, the N-doped $Ti_3C_2$ MXene has a sheet-like shape.

Figure 7A:
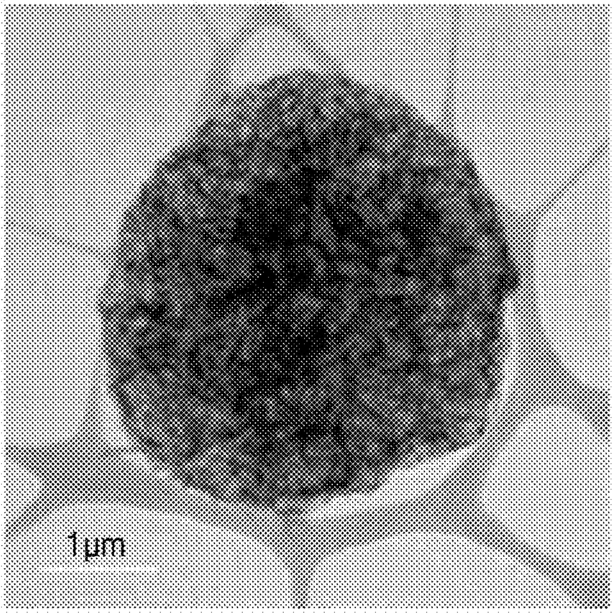
FIGS. 7A to 7D show TEM images of a 3D $MoC_2$@$Ti_3C_2$ MXene.
Figure 7B:
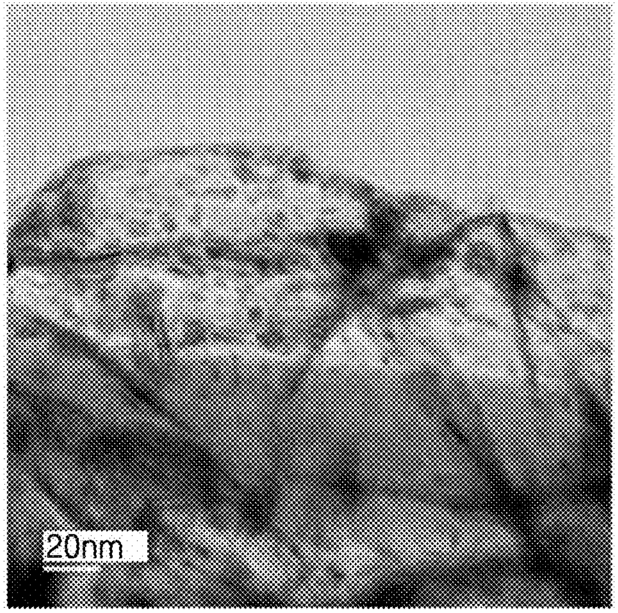
Figure 7C:
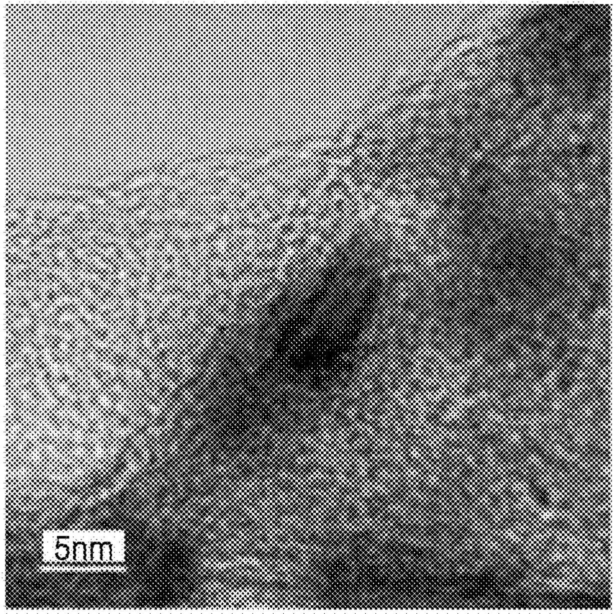
Figure 7D:
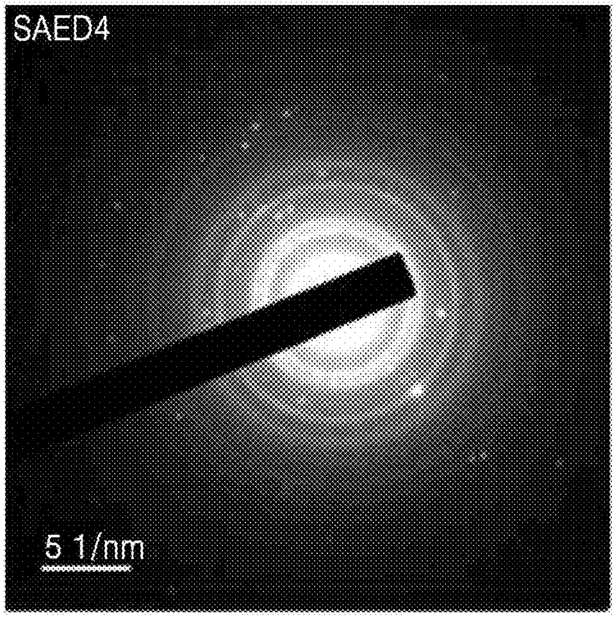
Figure 7E:
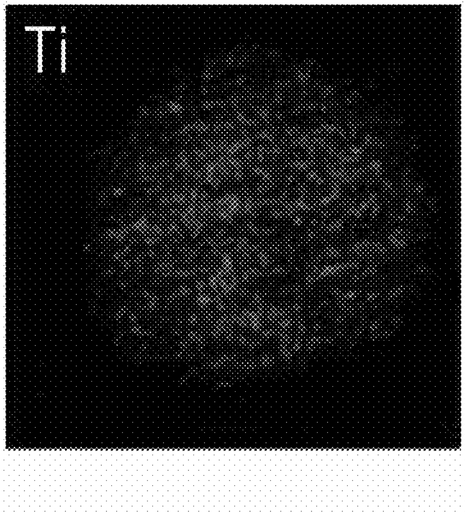
FIGS. 7E to 7H shows elemental mapping results of a 3D $MoC_2$@$Ti_3C_2$ MXene.
Figure 7F:
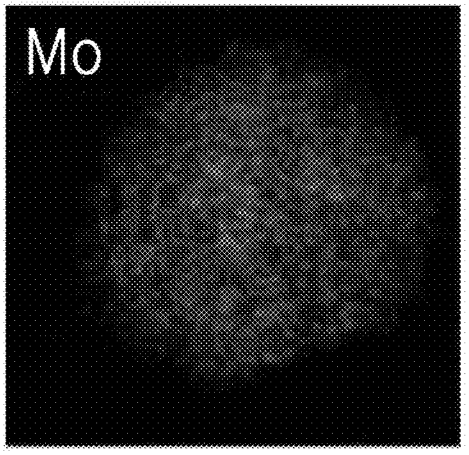
Figure 7G:
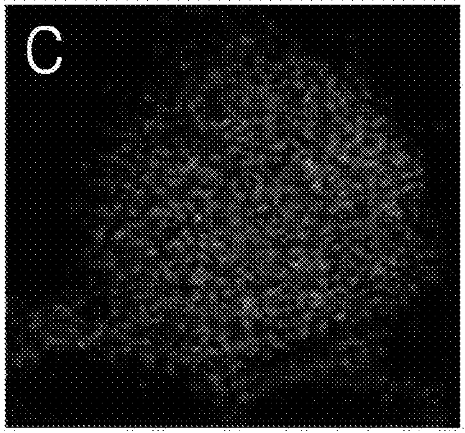
Figure 7H:
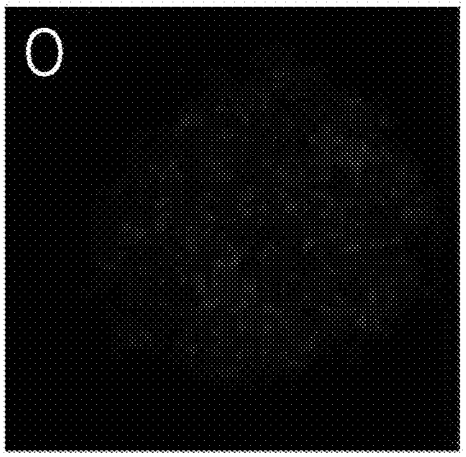

FIGS. 7A-7D show TEM images and FIGS. 7E-7F show elemental mapping data of a 3D $Mo_2C$@$Ti_3C_2$ MXene. In FIGS. 7A-7C, the 3D $Mo_2C$@$Ti_3C_2$ MXene has a spherical shape.

Figure 8:
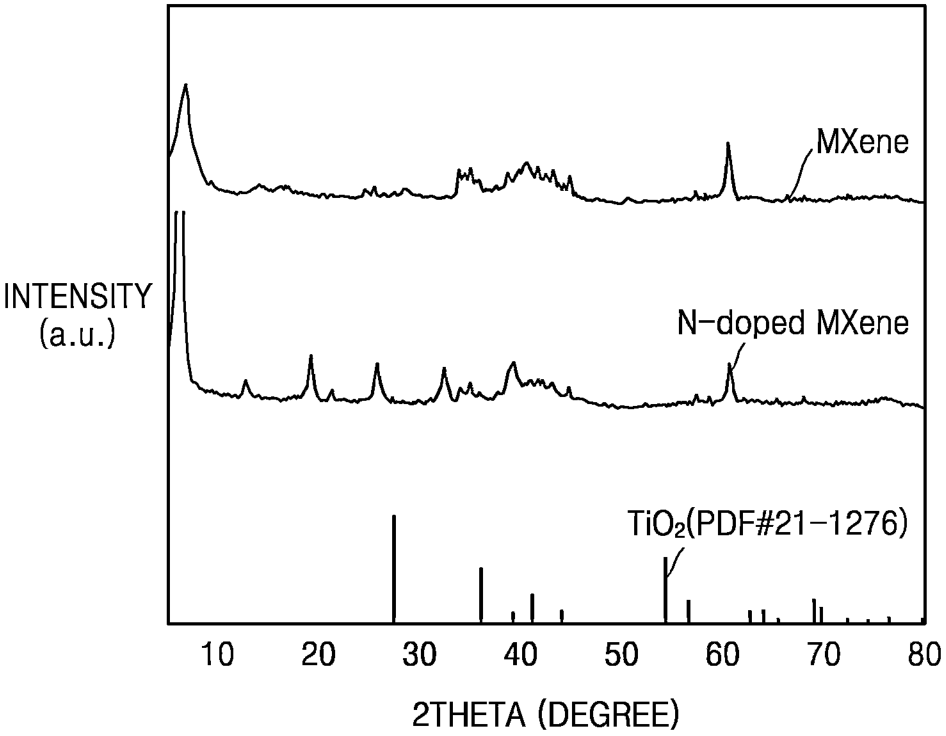
FIG. 8 is a graph of intensity (arbitrary units, a.u.) vs. 2theta (degree) showing X-ray diffraction (XRD) results of a $Ti_3C_2$ MXene, an N-doped $Ti_3C_2$ MXene, and a $TiO_2$ having a rutile structure.

FIG. 8 is a graph showing X-ray diffraction (XRD) data of a $Ti_3C_2$ MXene, an N-doped $Ti_3C_2$ MXene, and $TiO_2$ having a rutile structure.

Figure 9:
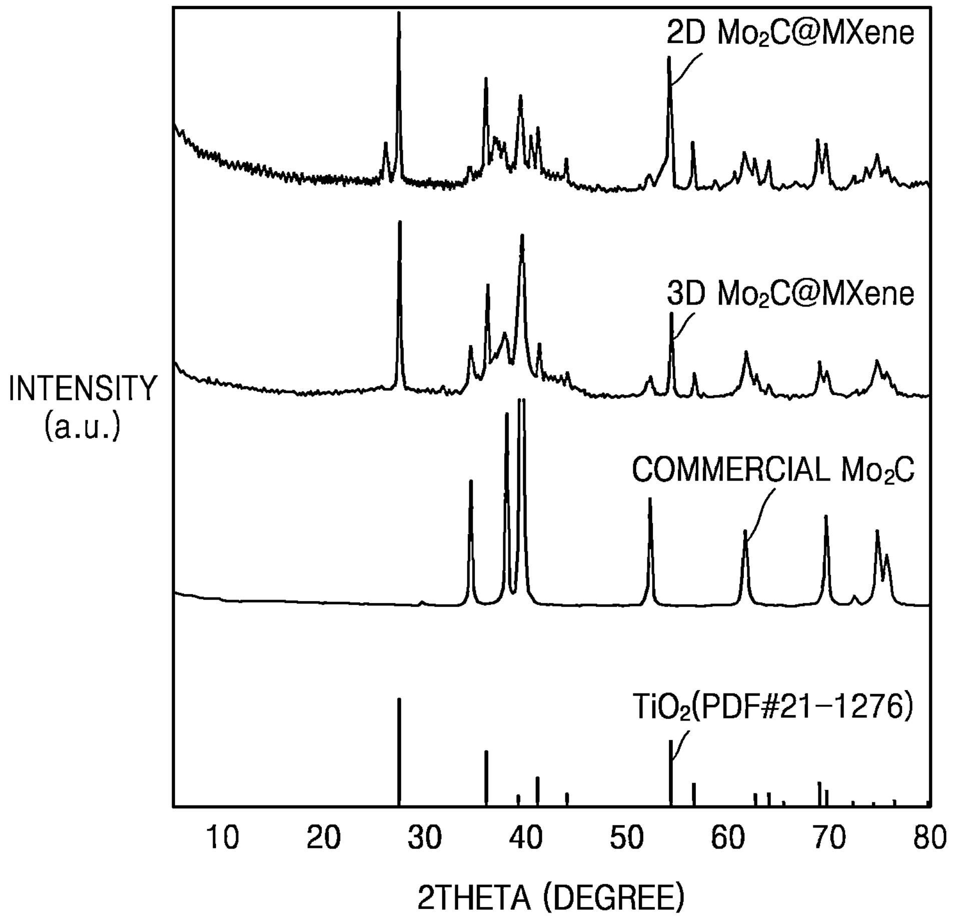
FIG. 9 is a graph of intensity (a.u.) vs. 2theta (degree) showing XRD results of a 2D $Mo_2C$@$Ti_3C_2$ MXene, a 3D $Mo_2C$@$Ti_3C_2$ MXene, a commercially available $Mo_2C$, and a $TiO_2$ having a rutile structure.

FIG. 9 is a graph showing XRD data of a 2D $Mo_2C$@$Ti_3C_2$ MXene, a 3D $Mo_2C$@$Ti_3C_2$ MXene, a commercially available $Mo_2C$, and $TiO_2$ having a rutile structure. As shown in FIG. 9, the 3D $Mo_2C$@$Ti_3C_2$ MXene had the characteristics of a spherical, three-dimensional shape compared to the 2D $Mo_2C$@$Ti_3C_2$ MXene.

In this Example, all XRD analyses were measured under Cu-Kα radiation (λ=1.5418 Å) conditions (XRD, X'Pert PRO).

Figure 10A:
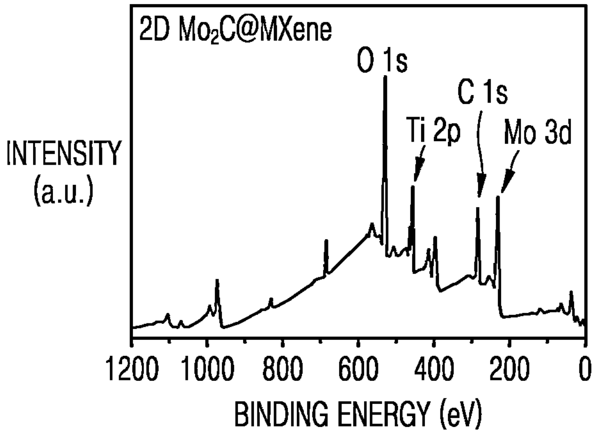
FIGS. 10A to 10D are each a graph of intensity (a.u.) vs. binding energy (electronvolts, eV) showing X-ray photoelectron spectroscopy (XPS) results of a 2D $Mo_2C$@$Ti_3C_2$ MXene, a 3D $Mo_2C$@$Ti_3C_2$ MXene, a N-doped $Ti_3C_2$ MXene, and a commercially available $Mo_2C$.
Figure 10B:
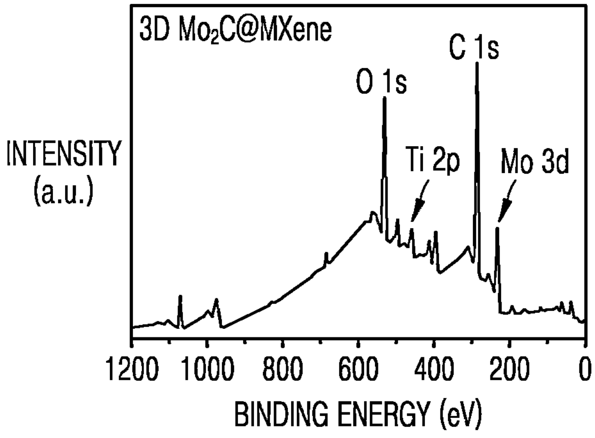
Figure 10C:
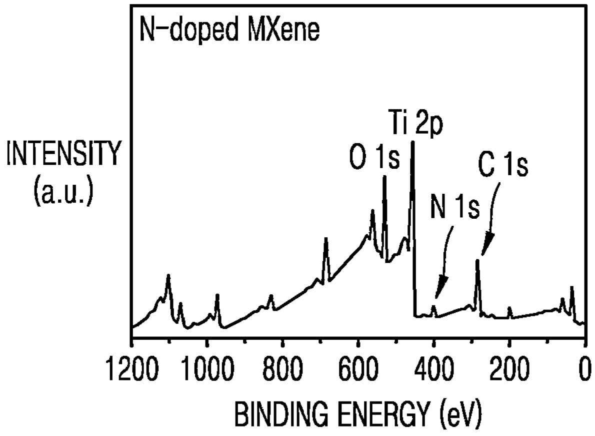
Figure 10D:
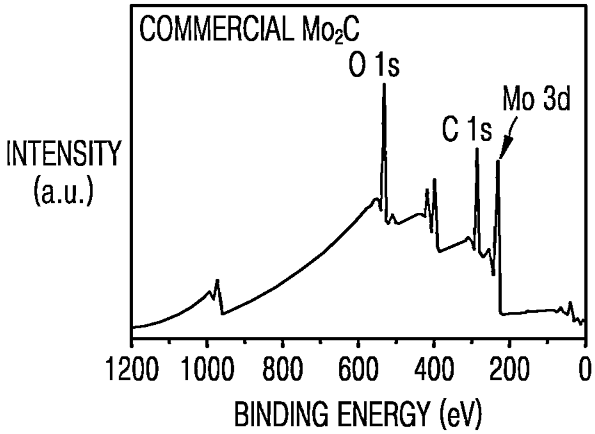

FIGS. 10A-10B are each a graph showing X-ray photoelectron spectroscopy (XPS) spectra of a 2D $Mo_2C$@$Ti_3C_2$ MXene, a 3D $Mo_2C$@$Ti_3C_2$ MXene, an N-doped $Ti_3C_2$ MXene, and a commercially available $Mo_2C$. As shown in FIG. 10, the 3D $Mo_2C$@$Ti_3C_2$ MXene had the characteristics of a spherical, three-dimensional shape compared to the 2D $Mo_2C$@$Ti_3C_2$ MXene.

To confirm the chemical bonds of the structures synthesized in this Example, all XPS analyses were performed using a K-Alpha device manufactured by Thermo Scientific.

Example 2: Enzyme Immobilization on Transition Metal Carbide/MXene Hybrid, Electrode Including Enzyme-Immobilized Transition Metal Carbide/MXene Hybrid, and Electroenzymatic Reduction Reaction Using Electrode In this Example, the N-doped $Ti_3C_2$ MXene, 2D $Mo_2C@Ti_3C_2$ MXene hybrid, 3D $Mo_2C@Ti_3C_2$ MXene hybrid, 2D $W_2C@Ti_3C_2$ MXene hybrid, and 3D $W_2C@Ti_3C_2$ MXene hybrid (hereinafter referred to 'nanoparticles') prepared in Example 1 were immobilized with an enzyme, and the reusability of the immobilized enzyme was confirmed. Also, the redox properties of oxide were confirmed using an enzyme-immobilized electrode and electrochemical devices including the same. Here, the enzyme was NosZ, and the oxide was $N_2O$.

(2.1) Enzyme Immobilization

By the enzyme immobilization, the surface of the nanoparticles was dual-functionalized by 3-aminopropyl-triethoxysilane (APTES) and glutaraldehyde (GA), and NosZ was immobilized on the dual-functionalized surface.

The APTES is an aminosilane frequently used for silanization. The silanization refers to functionalizing the surface with alkoxysilane. The APTES is one example, and any suitable (aminoalkyl)trialkoxysilane may be used instead of the APTES. An aminoalkyl group and a trialkoxy group may each have any carbon length, for example, 2 to 50 carbons, 2 to 30 carbons, 2 to 20 carbons, 3 to 50 carbons, 3 to 30 carbons, 3 to 20 carbons, 5 to 50 carbons, 5 to 30 carbons, or 5 to 20 carbons.

The GA is a molecule consisting of a 5-carbon chain with formyl groups at both ends. The GA has two carbonyl groups that are reactive with primary amine groups or hydrates thereof, and thus may act as a cross-linking agent for materials with primary amine groups, thereby forming imine-connected links. The GA is one example, and any suitable material with formyl groups at both ends having any carbon length, for example, 2 to 50 carbons, 2 to 30 carbons, 2 to 20 carbons, 3 to 50 carbons, 3 to 30 carbons, 3 to 20 carbons, 5 to 50 carbons, 5 to 30 carbons, or 5 to 20 carbons may be used.

First, the surface of the nanoparticles was hydroxylated by adding a 20% concentration of hydrogen peroxide solution.

Next, the hydroxylated surface of the nanoparticles was dual-functionalized by the APTES and GA. In detail, the nanoparticles were sonicated three times in ethanol each for 30 minutes, and then centrifuged at 13,000 rpm for 10 minutes to collect the nanoparticles. The collected nanoparticles were washed with distilled water three times to remove ethanol. In detail, distilled water was added to the collected nanoparticles, the mixture was then homogenized by creating a vortex, and a process of centrifugation at 13,000 rpm for 10 minutes was repeated three times.

10 mg of the nanoparticles and 2 volume % (v/v) APTES were added to toluene to prepare a suspension containing the nanoparticles and the APTES. The suspension was incubated at 250° C. for 12 to 15 hours with shaking at about 180 rpm to about 200 rpm. Next, the nanoparticles were washed three times in succession with acetone, ethanol, and distilled water. As a result, the nanoparticles in which the APTES was immobilized through OH groups on the surface of the nanoparticles were prepared.

10 mg of the resulting APTES-immobilized nanoparticles and the GA (1.0 M) were added to 100 mM phosphate salt buffer solution (pH 7.0) and incubated. As a result, the nanoparticles in which one functional group of the GA was connected to the APTES of the surface were obtained. The unbound GA molecules after the functionalization with the GA were removed by washing with a phosphate salt buffer solution (pH 7.0).

Next, an enzyme was immobilized on the GA-functionalized nanoparticles. In detail, the nanoparticles (5 mg to 10 mg) in the phosphate salt buffer solution (pH 7.0) and 1 mL of NosZ (0.5 mg to 1.0 mg protein) were mixed, and the mixture was incubated at 4° C. for 24 hours while shaking at 150 rpm. After the immobilization, the nanoparticles were collected by centrifugation, and then washed with 100 mM phosphate buffer solution (pH 7.0) three times. The protein concentration of the washed solution was measured using a Bradford method, and then the activity of the immobilized NosZ was measured.

An immobilization efficiency (IE) and an immobilization yield (IY) were calculated as follows:

$$IE\ (\%) = 100\% \times (\alpha i / \alpha f),$$

$$IY\ (\%) = 100\% \times [(\rho i - \rho w - \rho s) / \rho i],$$

wherein αi represents a total activity of the immobilized enzyme, αf represents a total activity of free enzyme, ρi represents a total protein content of a crude enzyme formulation, and ρw and ρs represent a protein concentrations in a washing solution and a supernatant after immobilization, respectively. All analyses were performed in triplicate.

Figure 11:
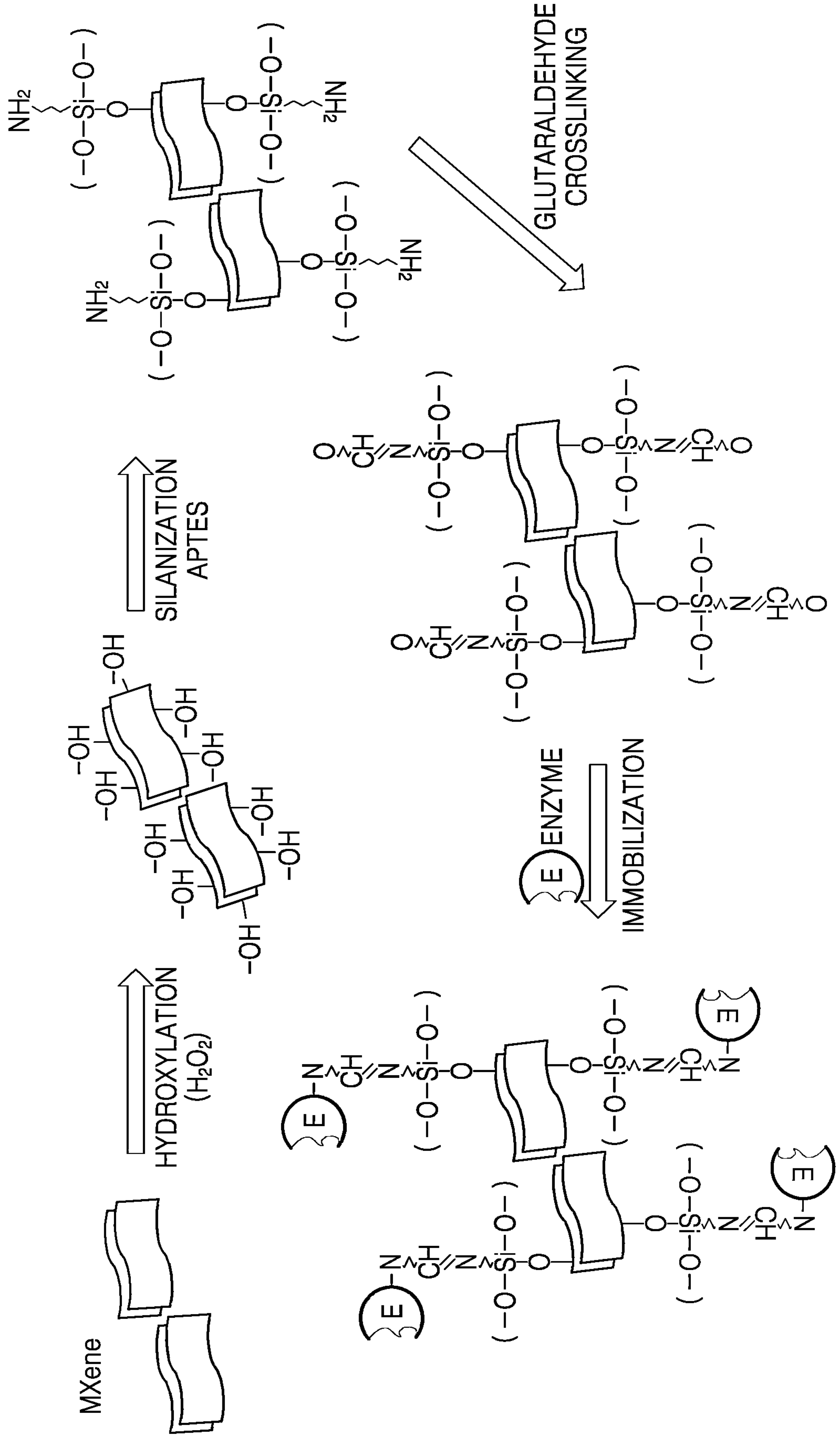
FIG. 11 is a diagram showing a process of dual-functionalizing the surface of nanoparticles with 3-aminopropyltriethoxysilane (APTES) and glutaraldehyde (GA) for enzyme immobilization.

FIG. 11 is a diagram showing the process of dual-functionalizing the surface of nanoparticles with APTES and GA for enzyme immobilization.

As a control, $SiO_2$ particles (from Sigma-Aldrich) were used instead of the nanoparticles prepared in the Examples. Table 1 shows the specific conditions for dual-functionalization of the nanoparticles.

TABLE 1

| Nanoparticles | Functionalization | Concentration |
|---|---|---|
| $SiO_2$ particles | APTES | 6% |
| | Glutaraldehyde | 1.0M |
| MXene derivative | APTES | 2% |
| | Glutaraldehyde | 1.0M |

(2.2) Immobilization Yield (IY) and Immobilization Efficiency (IE)

The IY (%) of the wild-type NosZ was calculated at different concentrations of GA (0.1 M, 0.5 M, 1.0 M, 1.25 M, and 1.50 M) and APTES (2%, 3%, 4%, and 6%). In the case of APTES, after functionalization of the $SiO_2$ particles and the MXene nanoparticles, the best results were obtained with IY (%) at 6% for the $SiO_2$ nanoparticles and at 2% for the remaining nanoparticles. In the case of GA, after functionalization of the $SiO_2$ particles and the MXene nanoparticles, the best results were obtained with IY (%) at 1 M concentration. According to these results, the optimal GA and APTES concentrations were used for additional experiments. For the dual-functionalized nanoparticles (10 mg), enzyme immobilization was performed at various enzyme concentrations from 0.25 mg/ml to 2 mg/mL (0.25 mg/mL, 0.50 mg/mL, 0.75 mg/mL, 1.00 mg/mL, 1.50 mg/mL, and 2.00 mg/mL).

Table 2 shows the IY and IE obtained for the wild-type NosZ immobilized on the functionalized nanoparticles.

TABLE 2

| Nanoparticles | Weight (mg) | NosZ (mg/mL) | IY (%) | IE (%) |
|---|---|---|---|---|
| $SiO_2$ | 10 | 1 | 78.44 | 97.36 |
| N-undoped $Ti_3C_2$ MXene | 10 | 1 | 60.57 | 101.2 |
| N-doped $Ti_3C_2$ MXene | 10 | 1 | 52.44 | 104.6 |
| 2D $Mo_2C$@$Ti_3C_2$ hybrid | 10 | 1 | 72.95 | 127.1 |
| 3D $Mo_2C$@$Ti_3C_2$ hybrid | 10 | 1 | 93.64 | 138.6 |
| 2D $W_2C$@$Ti_3C_2$ hybrid | 10 | 1 | 89.80 | 145.3 |
| 3D $W_2C$@$Ti_3C_2$ hybrid | 10 | 1 | 92.14 | 161.5 |

As shown in Table 2, regarding the IY (%), the IY (%) for the transition metal carbide/$Ti_3C_2$ hybrid was significantly greater than that for the $SiO_2$ nanoparticles and the $Ti_3C_2$ MXene nanoparticles with or without N-doping. Also, regarding the IE (%), the IE (%) for the transition metal carbide/$Ti_3C_2$ hybrid was significantly greater than that for the $SiO_2$ nanoparticles and the $Ti_3C_2$ MXene nanoparticles with or without N-doping.

Since the IY and IE for the transition metal carbide/$Ti_3C_2$ hybrid were significantly excellent, the enzyme stability, i.e., reusability of the enzyme, was confirmed.

(2.3) Reusability of NosZ Immobilized on MXene Support Phase

The reusability of NosZ immobilized on a 10 MXene support phase was measured in a phosphate buffer solution (100 mM, pH 7.13) at 25° C. over 10 cycles. After each reduction cycle, the immobilized enzyme was collected, centrifuged at 13,000 rpm for 15 minutes, and then washed with a phosphate salt buffer solution. In subsequent cycles, the immobilized enzyme was resuspended in a fresh buffer solution. An activity of the immobilized enzyme was considered 100% at the initial (first) cycle, and a relative activity of a subsequent cycle was calculated based on the activity of the initial cycle. Each period is defined as the complete reduction of a mediator benzyl viologen (BV). All analyses were performed in triplicate.

Figure 12:
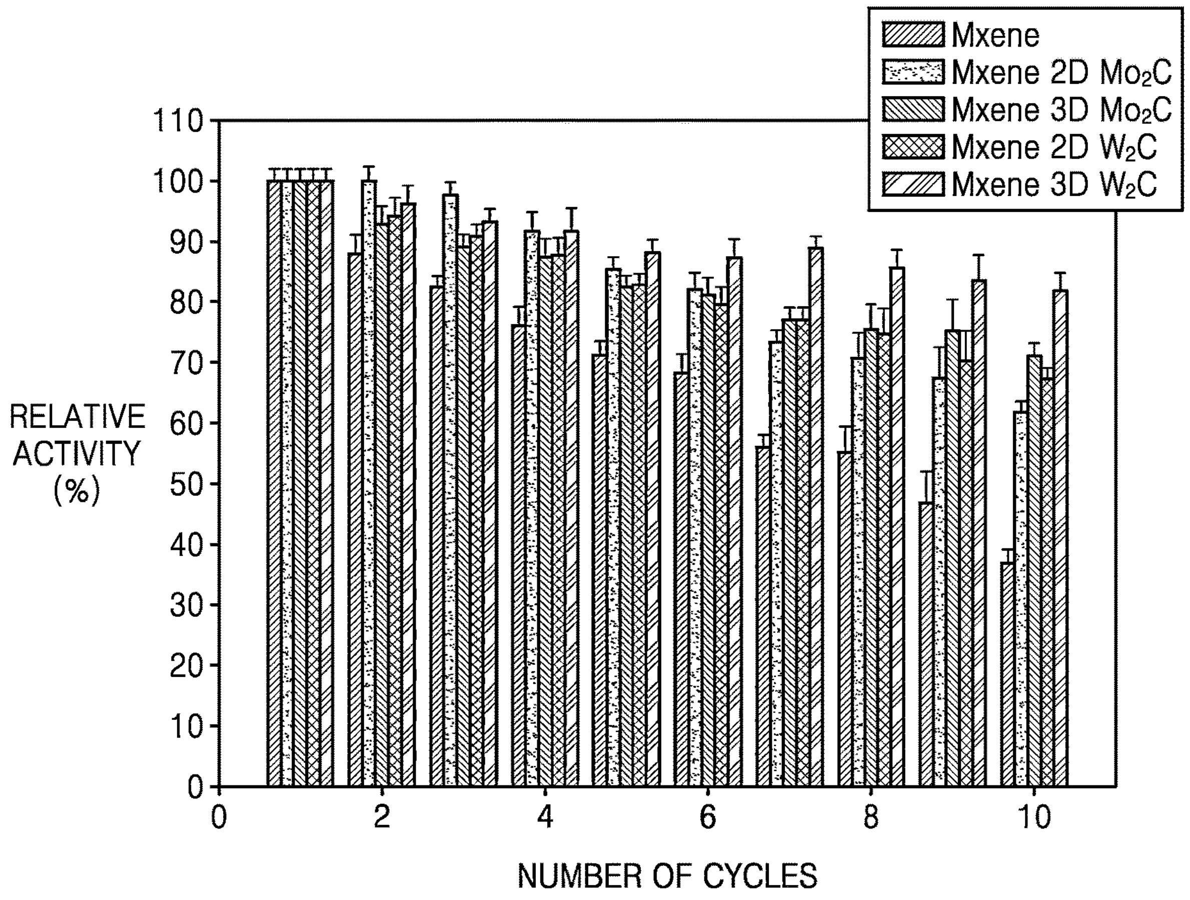
FIG. 12 is a histogram of relative activity (percent, %) vs. number of cycles (number) showing the reusability of wild-type nitrous oxide reductase gene (NosZ) immobilized on different nanoparticles.

FIG. 12 is a histogram of relative activity (%) vs. number of cycles, showing the reusability of the wild-type NosZ immobilized on different nanoparticles. As shown in FIG. 12, the NosZ immobilized on each of MXene, MXene 2D $Mo_2C$, MXene 3D $Mo_2C$, MXene 2D $W_2C$, and MXene 3D $W_2C$ maintained the activity of 43.89%, 61.67%, 71.09%, 67.11%, and 79.80%, after 10 cycles of reuse, respectively. Among all immobilization systems, the MXene 3D $W_2C$ showed the greatest reusability.

Table 3 shows the reusability of the wild-type NosZ immobilized on MXene, 2D $Mo_2C$@MXene, 3D $Mo_2C$@MXene, 2D $W_2C$@MXene, and 3D $W_2C$@MXene. Here, the MXene was N-doped $Ti_3C_2$ MXene.

TABLE 3

| | Relative activity (%) | | | | |
|---|---|---|---|---|---|
| Cycle | MXene | 2D $Mo_2C$ @MXene | 3D $Mo_2C$ @MXene | 2D $W_2C$ @MXene | 3D $W_2C$ @MXene |
| 1 | 100 | 100 | 100 | 100 | 100 |
| 2 | 93.13 | 99.30 | 92.92 | 94.15 | 95.27 |
| 3 | 88.41 | 97.78 | 89.08 | 90.80 | 90.45 |
| 4 | 81.11 | 91.88 | 87.31 | 87.69 | 88.63 |
| 5 | 76.39 | 85.60 | 82.59 | 82.76 | 85.22 |
| 6 | 73.39 | 81.91 | 81.20 | 79.38 | 84.22 |
| 7 | 66.09 | 73.43 | 77.28 | 77.23 | 82.98 |
| 8 | 61.37 | 70.84 | 75.51 | 74.80 | 81.62 |
| 9 | 51.98 | 67.52 | 75.22 | 70.15 | 80.68 |
| 10 | 42.11 | 61.67 | 71.09 | 67.11 | 79.80 |

As shown in Table 3, the NosZ immobilized on the transition metal carbide/MXene hybrid showed significantly excellent reusability.

(2.4) Electroenzymatic $N_2O$ Reduction

An electrochemical device including a conventional three-electrode cell was fabricated inside an anaerobic chamber, and the electrochemical properties related to the reduction of $N_2O$ to $N_2$ were measured by the electrochemical device.

Figure 13:
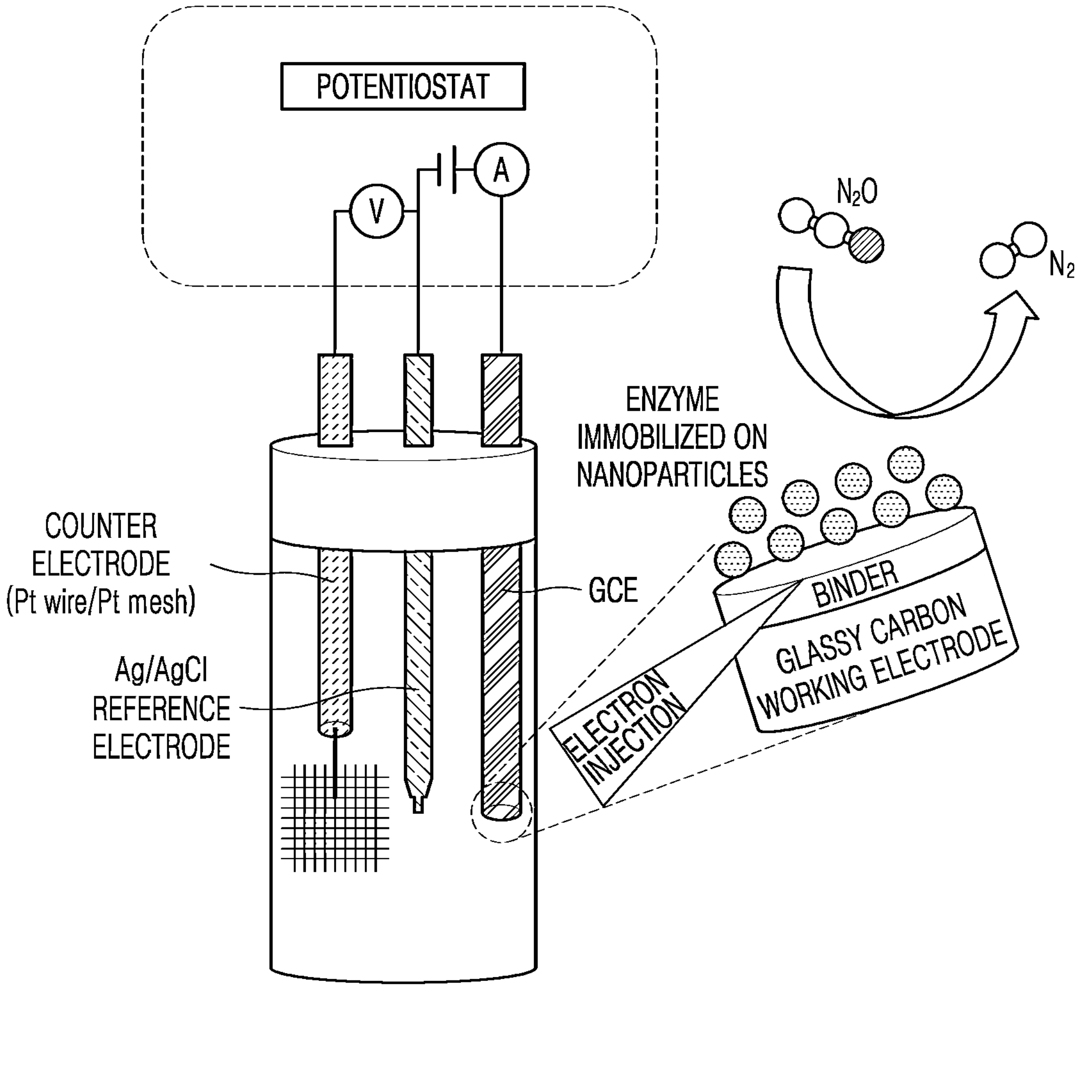
FIG. 13 is a diagram showing a potentiostat including a conventional three-electrode cell comprising a platinum counter electrode, a glassy carbon working electrode (GCE), and a Ag/AgCl reference electrode (+199 mV vs SHE)

FIG. 13 is a diagram showing a potentiostat including a conventional three-electrode cell comprising a platinum counter electrode, a glassy carbon working electrode (GCE), and Ag/AgCl reference electrode (±199 mV vs SHE). The SHE refers to a standard hydrogen electrode. In the GCE, the nanoparticles of the MXene on which an enzyme is immobilized or the nanoparticles of the transition metal carbide/MXene hybrid are immobilized through a binder.

As the NosZ, a wild-type NosZ derived from *Pseudomonas stutzeri* was used, and was activated anaerobically in a glove box using reduced benzyl viologen. Before the immobilization, the NosZ was incubated at room temperature for 180 minutes in a degassed solution containing 3.0 mM benzyl viologen (BV and 1.5 mM dithionite (DT) in 100 mM PBS buffer (pH 7.1). Excess reducing agent (e.g., DT) was removed by using His-tag affinity chromatography, and the eluted sample was collected, concentrated, and equilibrated with 100 mM PBS at pH 7.1, and then stored at 4° C. until further use.

For electrochemical studies, a glassy carbon electrode was first prepared by polishing with 0.05 micrometer (μm) alumina slurry, and a work electrode was prepared by drop-casting a 10 mM di-dodecyl di-methylammonium bromide (DDAB) binder (10 microliters, μL) and depositing NosZ that is either free or immobilized on the MXene or a derivative thereof, i.e., the N-, P-, or S-doped MXene or the TMC@MXene, at 4° C. A 100 mM phosphate buffer (pH 7.1) solution was used with 5 mM BV as a mediator, and a 10 mM $N_2O$ substrate was used as an electrolyte solution to convert $N_2O$ to $N_2$ by applying a current thereto. During the experiment, argon was purged into the electrolyte solution to establish anaerobic conditions.

While not wishing to be bound by theory, a proposed reaction pathway using an electrochemical enzyme catalyst may include a reaction pathway utilizing a mediator. For example, the mediator BV may donate electrons to the NosZ. A proposed electrochemical enzyme catalytic pathway may involve reduction of BV at an electrode via heterogeneous electron transfer (step 1). The NosZ may be reduced by BV (step 2) (from a dormant state of the inactive period (1 copper site (Cu II)/3 Cu I) to a fully reduced state (4 Cu I)), which can reduce $N_2O$ to $N_2$ (step 3).

Figure 14:
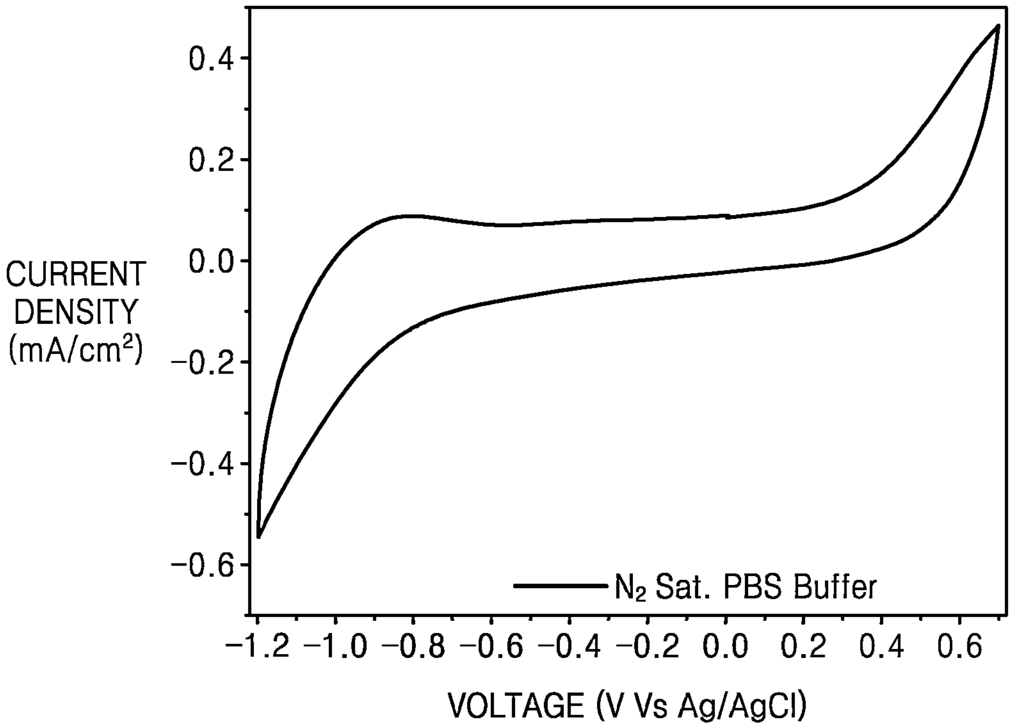
FIG. 14 is a graph of current density (milliampere per square centimeter, $mA/cm^2$) vs. voltage (volts (V) vs. Ag/AgCl) showing a cyclic voltammogram (CV) of a glassy carbon (GC) electrode loaded with NosZ activated at a sweep rate of 10 millivolts per second ($mV\ s^{-1}$) in 10 millimolar (mM) $N_2O$ solution in 100 mM phosphate buffered saline (PBS) buffer as an electrolyte at pH 7.

FIG. 14 is a diagram showing a cyclic voltammogram (CV) of a glassy carbon (GC) electrode loaded with NosZ activated at a sweep rate of 10 mV $s^{-1}$ in 10 mM $N_2O$ solution in 100 mM PBS buffer as an electrolyte at pH 7.

As shown in FIG. 14, the CV results (potentiometric experiments) of a GC electrode loaded with NosZ activated in the presence of $N_2O$ substrate indicated the presence of two redox pairs: signal 1 with a positive electrode peak (Epc I) and a positive electrode counterpart (Epa I); and a second positive electrode peak at a lower potential (Epc II) and a negative electrode counterpart (Epa II).

Three negative electrode reduction peaks were observed for Epc I, Epc II, and Epc III at 61 mV, −384 mV, and −702 mV, respectively, and the positive electrode counterparts showed only two positive electrode oxidation peaks, Epa I and Epa II, at 124 mV and −175 mV, respectively.

As a result of comparison with an electrode in the absence of substrate as a control, the control had no positive electrode peak Epa II obtained at −175 mV. Both a reduction peak on the positive electrode and an oxidation peak on the negative electrode were shown, indicating a reversible reaction. Likewise, the catalytic current density of the activated enzyme on the positive electrode increased in the presence of the $N_2O$ substrate.

Figure 15:
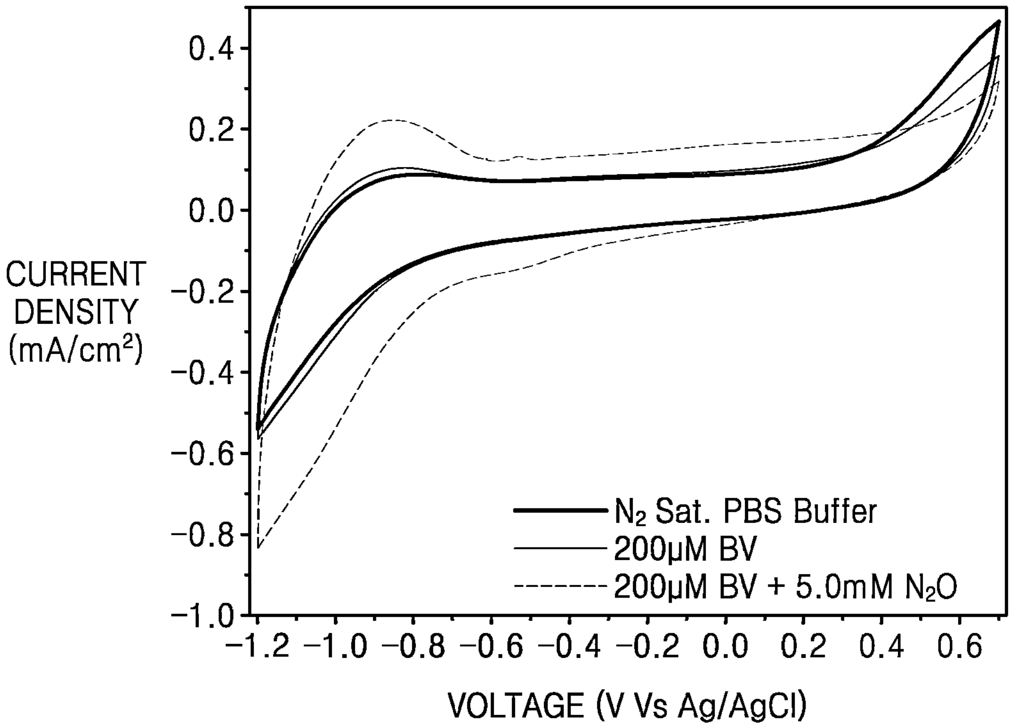
FIG. 15 is a graph of current density ($mA/cm^2$) vs. voltage (V vs. Ag/AgCl) showing CV results of purified NosZ (potential window in a range of 0.8 V to −0.8 V)

FIG. 15 is a graph showing CV results of a purified NosZ (potential window in a range of 0.8 V to −0.8 V).

Figure 16:
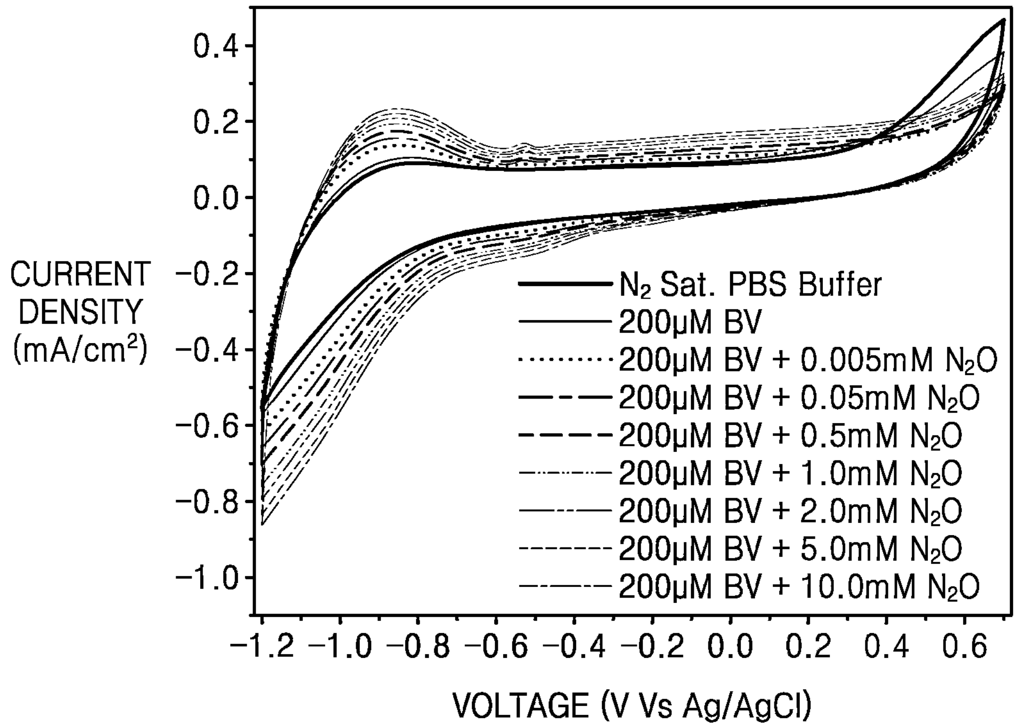
FIG. 16 is a graph of current density ($mA/cm^2$) vs. voltage (V vs. Ag/AgCl) showing CV results of activated NosZ (potential window in a range of 0.8 V to −1.2 V).

FIG. 16 is a graph showing CV results of an activated NosZ (potential window in a range of 0.8 V to −1.2 V). Each experiment was performed under the following conditions: $N_2$-saturated 100 M PBS buffer, 10 mM $N_2O$ substrate, 10 mM $N_2O$ substrate containing 5 mM BV, and 5 mM BV without substrate.

As shown in FIG. 16, the activated enzyme showed a dramatic increase in catalytic current compared to the inactivated enzyme (see FIG. 15) in the presence of 10 mM $N_2O$ substrate containing 5 mM BV. The electroenzymatic conversion of $N_2O$ to $N_2$ using the device can be a promising platform due to advantages of high activity, low cost, high selectivity, and environmental friendliness.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. An electrode for use in reducing $N_2O$ to $N_2$, the electrode comprising a MXene, or a derivative thereof, of formula $M_{n+1}X_nT_s$, wherein M is a transition metal of Groups 3, 4, 5, 6, or a combination thereof, of the Periodic Table of the Elements, wherein the transition metal is an early transition metal selected from Sc, Ti, V, Cr, Zr, Nb, Mo, Hf, Ta, or W, X is carbon, nitrogen, or a combination thereof, T is oxide, epoxide, hydroxide, C1-C5 alkoxide, fluoride, chloride, bromide, iodide, or a combination thereof, n is 1, 2, or 3, and s is 0, 1, or 2, and nitrous oxide reductase (NosZ) immobilized on the MXene or a derivative thereof, wherein the derivative is N-, P-, or S-doped MXene, or a hybrid material of the transition metal carbide and either of MXene, or N-, P-, or S-doped MXene.

2. The electrode of claim 1, wherein the MXene or a derivative thereof is immobilized on a surface of the electrode through a binder.

3. The electrode of claim 1, wherein the derivative is N-, P-, or S-doped $Ti_3C_2$ MXene, a hybrid material of $Mo_2C$ and $Ti_3C_2$ MXene, a hybrid material of $Mo_2C$ and N-, P-, or S-doped $Ti_3C_2$ MXene, a hybrid material of $W_2C$ and $Ti_3C_2$ MXene, or a hybrid material of $W_2C$ and N-, P-, or S-doped $Ti_3C_2$ MXene.

4. The electrode of claim 1, wherein the MXene or a derivative thereof has a three-dimensional structure in which delaminated nanosheets comprise 2 to 10 interlaced layers, and optionally wherein the MXene is $Ti_3C_2$ MXene.

5. The electrode of claim 1, wherein the nitrous oxide reductase is cross-linked to a carbon compound having two or more formyl groups on an immobilized silanized surface.

6. An apparatus for use in reducing $N_2O$ to $N_2$, the apparatus comprising a working electrode, a counter electrode, and a reference electrode, wherein the working electrode is the electrode of claim 1.

7. A method of reducing $N_2O$ to $N_2$, the method comprising:

contacting $N_2O$ or a dissolved form thereof in a liquid medium with the electrode of claim 1; and applying a current to the electrode.

8. The method of claim 7, wherein the contacting is performed within the apparatus of claim 6.

* * * * *